(12) United States Patent
Witt et al.

(10) Patent No.: US 12,102,794 B2
(45) Date of Patent: Oct. 1, 2024

(54) CATHETER DRESSING AND/OR SECUREMENT DEVICE AND SYSTEM, METHOD, AND PRODUCT FOR INTRAVENOUS SITE CONDITION DETECTION

(71) Applicant: Becton, Dickinson and Company, Franklin Lakes, NJ (US)

(72) Inventors: Erik Kurt Witt, Oakland, NJ (US); Ashley Rachel Rothenberg, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 203 days.

(21) Appl. No.: 17/469,254

(22) Filed: Sep. 8, 2021

(65) Prior Publication Data

US 2022/0072226 A1 Mar. 10, 2022

Related U.S. Application Data

(60) Provisional application No. 63/076,204, filed on Sep. 9, 2020.

(51) Int. Cl.
*A61M 5/168* (2006.01)
*A61M 5/14* (2006.01)
(Continued)

(52) U.S. Cl.
CPC .... *A61M 5/16836* (2013.01); *A61M 5/14248* (2013.01); *A61M 25/02* (2013.01);
(Continued)

(58) Field of Classification Search
CPC .......... A61M 5/16836; A61M 5/14248; A61M 25/02; A61M 2005/1403;
(Continued)

(56) References Cited

U.S. PATENT DOCUMENTS

| 5,546,955 A * | 8/1996 | Wilk | A61B 5/6807 |
| | | | 600/592 |
| 2006/0047218 A1 * | 3/2006 | Bloom | A61B 5/413 |
| | | | 128/903 |

(Continued)

OTHER PUBLICATIONS

Silvah et al., "Body surface infrared thermometry in patients with central venous cateter-related infections", Einstein, 2015, pp. 364-369, vol. 13:3.

*Primary Examiner* — Kami A Bosworth
*Assistant Examiner* — Avery Smale
(74) *Attorney, Agent, or Firm* — The Webb Law Firm

(57) ABSTRACT

A method may include obtaining, with a first temperature sensor, a first temperature measurement at a first location on a body of a patient adjacent a catheter insertion site of a catheter; obtaining, with an array of temperature sensors, a plurality of temperature measurements at a plurality of locations on the body of the patient, each of the plurality of locations being spaced apart from the first location, and the plurality of locations including locations at a plurality of different distances from the first location; determining, with at least one processor, based on the first temperature measurement and the plurality of temperature measurements, an alert condition associated with a dressing and/or securement device and/or the catheter; and in response to determining the alert condition, generating, with at least one processor, an alert to a user.

20 Claims, 12 Drawing Sheets

(51) Int. Cl.
*A61M 5/142* (2006.01)
*A61M 25/02* (2006.01)

(52) U.S. Cl.
CPC ............... *A61M 2005/1403* (2013.01); *A61M 2025/0266* (2013.01); *A61M 2205/0205* (2013.01); *A61M 2205/18* (2013.01); *A61M 2205/3368* (2013.01); *A61M 2230/50* (2013.01)

(58) Field of Classification Search
CPC .. A61M 2025/0266; A61M 2205/0205; A61M 2205/18; A61M 2205/3368; A61M 2230/50; A61M 2005/1588; A61M 2025/028; A61M 5/14244; A61M 2005/14264; A61M 2005/14272; A61M 5/172; A61M 5/1723; A61M 2005/1726; A61M 1/912; A61M 2025/0213; A61M 2025/024; A61M 2025/0273; A61M 2025/0286; A61F 2013/00953; A61F 2013/00421; A61F 2013/00417; A61F 2013/00412; A61F 13/05
See application file for complete search history.

(56) References Cited

U.S. PATENT DOCUMENTS

| | | |
|---|---|---|
| 2011/0071482 A1 | 3/2011 | Selevan |
| 2016/0000609 A1* | 1/2016 | Van Holten ....... A61F 13/00063 604/304 |
| 2019/0374162 A1 | 12/2019 | Ofek et al. |
| 2021/0236725 A1* | 8/2021 | Augustine ......... A61M 5/16836 |

* cited by examiner

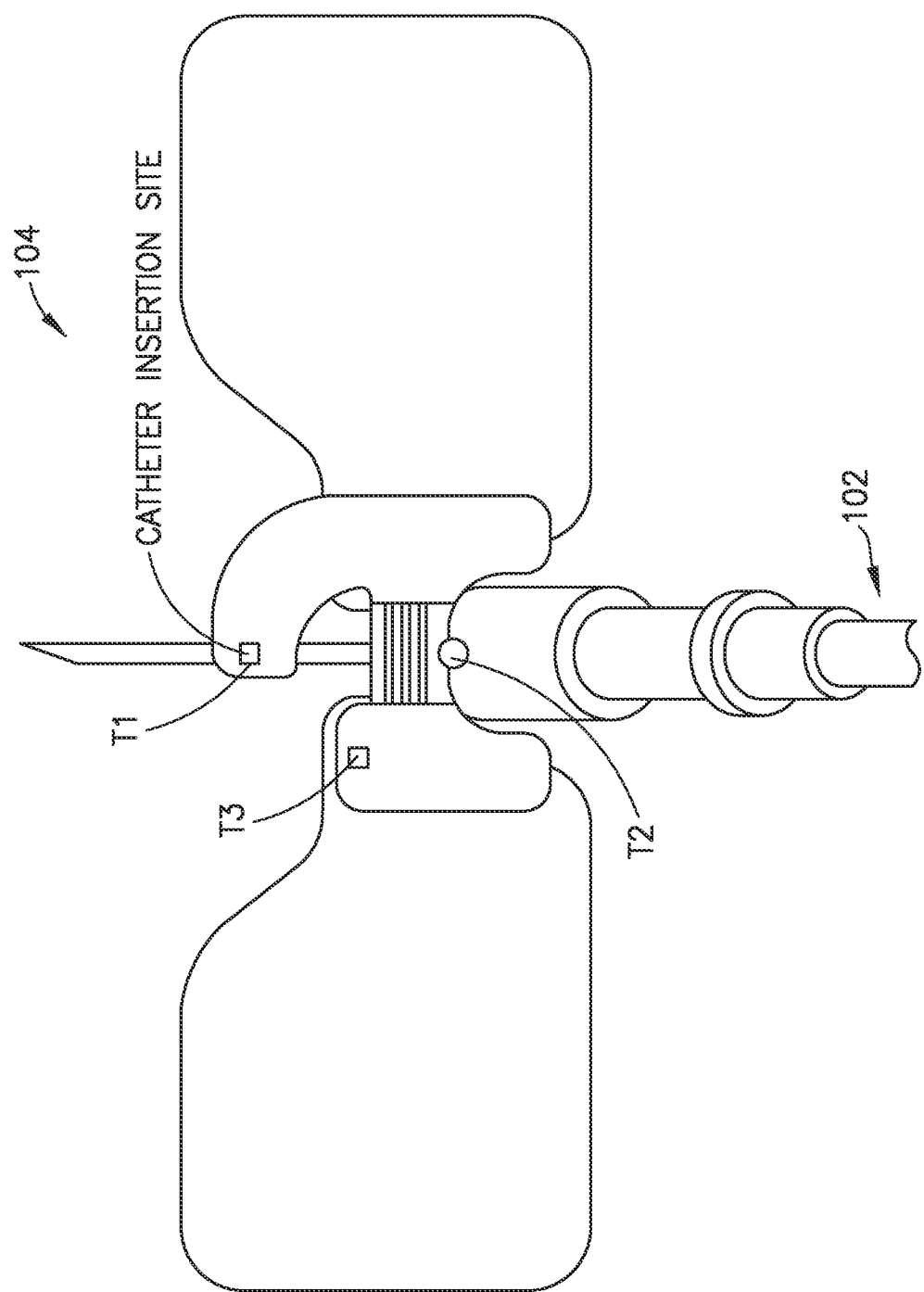

CATHETER DRESSING AND/OR SECUREMENT DEVICE AND SYSTEM, METHOD, AND PRODUCT FOR INTRAVENOUS SITE CONDITION DETECTION

CROSS-REFERENCE TO RELATED APPLICATION

The present application claims priority to U.S. Provisional Application No. 63/076,204, entitled "Catheter Dressing and/or Securement Device and System, Method, and Product for Intravenous Site Condition Detection", filed Sep. 9, 2020, the entire disclosure of which is hereby incorporated by reference in its entirety.

BACKGROUND

1. Field

The present disclosure relates generally to a dressing and/or securement device for a catheter and, in some non-limiting embodiments or aspects, to systems, devices, products, apparatus, and/or methods for temperature sensing for intravenous site condition detection.

2. Technical Considerations

Infected catheters have demonstrated increased temperature at a catheter insertion site compared to body surface temperature. Clinically, the body has an inflammatory reaction to the catheter which can raise the local temperature around the catheter insertion site at which the catheter enters the skin. There can be many other sources of local temperature difference related to catheters, such as reactions to drugs introduced by the catheter, fluids leaked outside the vein (e.g. infiltration, extravasation, etc.), reactions to pistoning or mechanical catheter motion in the body, immune responses to infectious agents such as bacteria and biofilms that form on the catheter surface or inside the lumen, the temperature of the IV fluid relative to the body or ambient temperature, foreign body reactions to the catheter materials and surface, and/or the like.

Silvah J H, Lima C M, Unamuno Mdo R, Schetino M A, Schetino L P, Fassini P G, Brandão CF, Basile-Filho A, Cunha S F, and Marchini J S disclose in their paper titled "Body surface infrared thermometry in patients with central venous catheter-related infections", Einstein, (Sao Paulo), 2015 July-September, 13(3):364-9, doi: 10.1590/S1679-45082015AO3397, the contents of which is hereby incorporated by reference in its entirety, evidence of temperature difference relative to a catheter insertion site indicating an infection. Further, increased temperature at a catheter insertion site may be due to both infection and phlebitis or other irritation to the vein caused by the catheter or a fluid running through the catheter. Additionally, decreases in temperature at a catheter insertion site may also indicate a problem because these decreases in temperature may be caused when fluid leaks into the tissue from the infusion. This leaked fluid can lead to outcomes as minor as pain or, in some cases, tissue damage resulting in loss of a limb. Moreover, the catheter tubing and the fluid running therethrough may provide a source of temperature variation because the fluid being delivered is often at room temperature or chilled as opposed to being at a body temperature of the patient.

Accordingly, there is a need in the art for improved temperature sensing for intravenous site condition detection.

SUMMARY

Accordingly, provided are improved systems, devices, products, apparatus, and/or methods for temperature sensing for intravenous site condition detection.

According to some non-limiting embodiments or aspects, provided is a method including: obtaining, with a first temperature sensor of a dressing and/or securement device for a catheter, a first temperature measurement at a first location on a body of a patient adjacent a catheter insertion site of the catheter; obtaining, with an array of temperature sensors of the dressing and/or securement device, a plurality of temperature measurements at a plurality of locations on the body of the patient, each of the plurality of locations being spaced apart from the first location, and the plurality of locations including locations at a plurality of different distances from the first location; determining, with at least one processor, based on the first temperature measurement and the plurality of temperature measurements, an alert condition associated with the dressing and/or securement device and/or the catheter; and in response to determining the alert condition, generating, with at least one processor, an alert to a user.

In some non-limiting embodiments or aspects, the method further includes: obtaining, with a second temperature sensor of the dressing and/or securement device, a second temperature measurement at a catheter tubing of the catheter; and determining, with at least one processor, based on the first temperature measurement, the second temperature measurement, and the plurality of temperature measurements, an alert condition associated with the dressing and/or securement device and/or the catheter.

According to some non-limiting embodiments or aspects, provided is a system including: a dressing and/or securement device for a catheter including: a first temperature sensor configured to obtain a first temperature measurement at a first location on a body of a patient adjacent a catheter insertion site of the catheter on the body of the patient; and an array of temperature sensors configured to obtain a plurality of temperature measurements at a plurality of locations on the body of the patient, each temperature sensor of the array of temperature sensors being spaced apart from the first temperature sensor, and the array of temperature sensors including temperature sensors at a plurality of different distances from the first temperature sensor; and one or more processors programmed and/or configured to: determine, based on the first temperature measurement and the plurality of temperature measurements, an alert condition associated with the dressing and/or securement device and/ or the catheter; and in response to determining the alert condition, generate an alert to a user.

In some non-limiting embodiments or aspects, the dressing and/or securement device further includes a second temperature sensor, the second temperature sensor being configured to obtain a second temperature measurement at a catheter tubing of the catheter, the second temperature sensor being spaced apart from the first temperature sensor and the array of temperature sensors, and the one or more processors being further programmed and/or configured to: determine, based on the first temperature measurement, the second temperature measurement, and the plurality of temperature measurements, an alert condition associated with the dressing and/or securement device and/or the catheter.

According to some non-limiting embodiments or aspects, provided is a dressing and/or securement device for a catheter including: a support member including: a first temperature sensor configured to obtain a first temperature measurement at a first location on a body of a patient adjacent a catheter insertion site of the catheter; and an array of temperature sensors configured to obtain a plurality of temperature measurements at a plurality of locations on the body of the patient, each temperature sensor of the array of temperature sensors being spaced apart from the first temperature sensor on the support member, and the array of temperature sensors including temperature sensors at a plurality of different distances from the first temperature sensor; and a wired or wireless communication device configured to communicate the first temperature measurement and the plurality of temperature measurements to one or more processors.

In some non-limiting embodiments or aspects, the support member further includes a second temperature sensor, the second temperature sensor being configured to obtain a second temperature measurement at a catheter tubing of the catheter, the second temperature sensor being spaced apart from the first temperature sensor and the array of temperature sensors on the support member, and the wired or wireless communication device being configured to communicate the first temperature measurement, the second temperature measurement, and the plurality of temperature measurements to one or more processors.

According to some non-limiting embodiments or aspects, provided is a computer program product including at least one non-transitory computer-readable medium including program instructions that, when executed by at least one processor, cause the at least one processor to: obtain a first temperature measurement associated with a first location on a body of a patient adjacent a catheter insertion site of a catheter on the body of the patient; obtain a plurality of temperature measurements associated with a plurality of locations on the body of the patient, each of the plurality of locations being spaced apart from the first location, and the plurality of locations including locations at a plurality of different distances from the first location; determine, based on the first temperature measurement and the plurality of temperature measurements, an alert condition associated with the catheter and/or a dressing and/or securement device for the catheter; and in response to determining that the at least one threshold is satisfied, generate an alert to a user.

In some non-limiting embodiments or aspects, the instructions further cause the at least one processor to obtain a second temperature measurement associated with a catheter tubing of the catheter; and determine, based on the first temperature measurement, the second temperature measurement, and the plurality of temperature measurements, an alert condition associated with the catheter and/or a dressing and/or securement device for the catheter.

Further embodiments or aspects are set forth in the following numbered clauses:

Clause 1. A method comprising: obtaining, with a first temperature sensor of a dressing and/or securement device for a catheter, a first temperature measurement at a first location on a body of a patient adjacent a catheter insertion site of the catheter; obtaining, with an array of temperature sensors of the dressing and/or securement device, a plurality of temperature measurements at a plurality of locations on the body of the patient, wherein each of the plurality of locations is spaced apart from the first location, and wherein the plurality of locations includes locations at a plurality of different distances from the first location; determining, with at least one processor, based on the first temperature measurement and the plurality of temperature measurements, an alert condition associated with the dressing and/or securement device and/or the catheter; and in response to determining the alert condition, generating, with at least one processor, an alert to a user.

Clause 2. The method of clause 1, further comprising: obtaining, with the first temperature sensor, a first reference measurement at the first location on the body of the patient; obtaining, with the array of temperature sensors, a plurality of reference measurements at the plurality of locations on the body of the patient; determining, with at least one processor, a plurality of first temperature differences between the first reference measurement and each of the plurality of reference measurements; determining, with at least one processor, a plurality of second temperature differences between a reference measurement at a most distant location of the plurality of locations from the first location and each reference measurement at each of the remaining locations of the plurality of locations; determining, with at least one processor, at least one threshold temperature based on the plurality of first temperature differences and the plurality of second temperature differences; determining, with at least one processor, that the first temperature measurement, one or more temperature measurements of the plurality of temperature measurements, or any combination thereof, satisfies the at least one threshold temperature; and in response to determining that the at least one threshold temperature is satisfied, generating the alert to the user.

Clause 3. The method of any of clauses 1 and 2, further comprising: determining, with at least one processor, that a temperature measurement of the plurality of temperature measurements at a most distant location of the plurality of locations from the first location satisfies a threshold temperature; and in response to determining that the temperature measurement at the most distant location of the plurality of locations from the first location satisfies the threshold temperature, generating, with at least one processor, the alert to the user, wherein the alert includes information associated with a potential peeling of the dressing and/or securement device.

Clause 4. The method of any of clauses 1-3, further comprising: determining, with at least one processor, that two or more temperature measurements of the first temperature measurement and the plurality of temperature measurements satisfy a threshold temperature; and in response to determining that the two or more temperature measurements of the first temperature measurement and the plurality of temperature measurements satisfy the threshold temperature, generating, with at least one processor, the alert to the user, wherein the alert includes information associated with a potential tunneling of the dressing and/or securement device.

Clause 5. The method of any of clauses 1-4, further comprising: determining, with at least one processor, that each temperature measurement of the first temperature measurement and the plurality of temperature measurements satisfies a threshold temperature; and in response to determining that each temperature measurement of the first temperature measurement and the plurality of temperature measurements satisfies the threshold temperature, generating, with at least one processor, the alert to the user, wherein the alert includes information associated with a potential removal of the dressing and/or securement device.

Clause 6. The method of any of clauses 1-5, further comprising: obtaining, with a second temperature sensor of the dressing and/or securement device, a second temperature measurement at a catheter tubing of the catheter; determining, with at least one processor, that a first change over time in the second temperature satisfies an infusion temperature threshold; storing, with at least one processor, a confirmation of an infusion operation in association with a record of the patient; determining, with at least one processor, a second change over time in the second temperature subsequent to the first change that satisfies a flush temperature threshold; and in response to determining that the second change over time in the second temperature satisfies the flush temperature threshold, generating, with at least one processor, the alert to the user, wherein the alert includes a prompt to the user to confirm delivery of a flushing fluid.

Clause 7. The method of any of clauses 1-6, further comprising: determining, with at least one processor, that at least one pattern of change in at least one of the following: the first temperature measurement, one or more temperature measurements of the plurality of temperature measurements, or any combination thereof, satisfies at least one threshold pattern of change; and in response to determining that the at least one pattern of change satisfies the at least one threshold pattern of change, generating, with at least one processor, the alert to the user, wherein the alert includes information associated with a potential issue with the dressing and/or securement device and/or the catheter.

Clause 8. The method of any of clauses 1-7, wherein the at least one pattern of change includes a change over time in one or more individual temperature measurements of the first temperature measurement and the plurality of temperature measurements.

Clause 9. The method of any of clauses 1-8, wherein the at least one pattern of change includes a change over time in a temperature difference between two or more temperature measurements of the first temperature measurement and the plurality of temperature measurements.

Clause 10. The method of any of clauses 1-9, further comprising: determining, with at least one processor, the at least one threshold pattern of change based on at least one of the following: a patient parameter associated with the patient, a medication parameter associated with a medication delivered, being delivered, or to be delivered to the patient, a care environment parameter associated with a care environment in which the patient is located, or any combination thereof.

Clause 11. The method of any of clauses 1-10, wherein the first location and a closest location of the plurality of locations to the first location are located at a same distance from a catheter tubing of the catheter and a same distance from the catheter insertion site of the catheter on the body of the patient, and wherein the method further comprises: determining, with at least one processor, that a change between the first temperature measurement and a temperature measurement of the plurality of temperature measurements at the closest location of the plurality of locations to the first location satisfies a threshold temperature; and in response to determining that the change between the first temperature measurement and the temperature measurement of the plurality of temperature measurements at the closest location of the plurality of locations to the first location satisfies the threshold temperature, generating, with at least one processor, the alert to the user, wherein the alert includes information associated with a potential issue with the dressing and/or securement device and/or the catheter.

Clause 12. The method of any of clauses 1-11, further comprising: determining, with at least one processor, at least one of (i) an increase in temperatures of temperature measurements from a most distant location of the plurality of locations to the first temperature measurement and (ii) an increase in a temperature difference between the first temperature measurement and a temperature measurement at the most distant location of the plurality of locations to the first temperature measurement that satisfies a threshold temperature increase; and in response to determining the at least one of (i) and (ii), generating, with at least one processor, the alert to the user, wherein the alert includes information associated with a potential issue with the dressing and/or securement device and/or the catheter.

Clause 13. The method of any of clauses 1-12, further comprising: obtaining, with a second temperature sensor of the dressing and/or securement device, a second temperature measurement at a catheter tubing of the catheter; determining, with at least one processor, that a decrease in temperature between the first location and a most distant location of the plurality of locations from the first location satisfies a threshold temperature; in response to determining that the decrease in temperature satisfies the threshold temperature, determining, with at least one processor, that a comparison of the first temperature measurement and at least one of the following: (i) the second temperature measurement at a current time and at least one time prior to the current time and (ii) a temperature measurement of a location of the plurality of locations more distant from the catheter insertion site than the first location, satisfy at least one threshold temperature; and in response to determining that the at least one threshold temperature is satisfied, generating, with at least one processor, the alert to the user, wherein the alert includes information associated with a potential issue with the dressing and/or securement device and/or the catheter.

Clause 14. The method of any of clauses 1-13, wherein the first temperature measurement and the plurality of temperature measurements are obtained at a periodic rate, and wherein the method further comprises: determining, with at least one processor, the periodic rate based on at least one of the following: a patient parameter associated with the patient, a medication parameter associated with a medication delivered, being delivered, or to be delivered to the patient, a care environment parameter associated with a care environment in which the patient is located, or any combination thereof.

Clause 15. The method of any of clauses 1-14, further comprising: obtaining, with a plurality of arrays of temperature sensors of the dressing and/or securement device, the plurality of temperature measurements at the plurality of locations on the body of the patient, wherein the plurality of arrays are spaced apart about the catheter insertion site.

Clause 16. The method of any of clauses 1-15, wherein the plurality of arrays is spaced apart around a circumference surrounding the catheter insertion site, and wherein locations of the plurality of locations associated with individual arrays of the plurality of arrays are spaced apart radially at a plurality of different distances from the catheter insertion site.

Clause 17. The method of any of clauses 1-16, wherein an array of the plurality of arrays includes the first temperature sensor.

Clause 18. The method of any of clauses 1-17, wherein the dressing and/or securement device includes a marking or opening indicating an orientation of the support member for attachment at the catheter insertion site of the catheter on the body of the patient, and wherein the marking or opening is aligned with the catheter insertion site of the catheter on the body of the patient.

Clause 19. The method of any of clauses 1-18, wherein the dressing and/or securement device includes a support member, wherein the support member includes the first temperature sensor and the plurality of temperature sensors, and wherein the support member further includes an adhesive layer.

Clause 20. The method of any of clauses 1-19, wherein the dressing and/or securement device includes an antimicrobial disk.

Clause 21. A system comprising: a dressing and/or securement device for a catheter including: a first temperature sensor configured to obtain a first temperature measurement at a first location on a body of a patient adjacent a catheter insertion site of the catheter on the body of the patient; and an array of temperature sensors configured to obtain a plurality of temperature measurements at a plurality of locations on the body of the patient, wherein each temperature sensor of the array of temperature sensors is spaced apart from the first temperature sensor, and wherein the array of temperature sensors includes temperature sensors at a plurality of different distances from the first temperature sensor; and one or more processors programmed and/or configured to: determine, based on the first temperature measurement and the plurality of temperature measurements, an alert condition associated with the dressing and/or securement device and/or the catheter; and in response to determining the alert condition, generate an alert to a user.

Clause 22. The system of clause 21, wherein the first temperature sensor is further configured to obtain a first reference measurement at the first location on the body of the patient, wherein the array of temperature sensors is further configured to obtain a plurality of reference measurements at the plurality of locations on the body of the patient, and wherein the one or more processors are further programmed and/or configured to: determine a plurality of first temperature differences between the first reference measurement and each of the plurality of reference measurements; determine a plurality of second temperature differences between a reference measurement at a most distant temperature sensor of the array of temperature sensors from the first temperature sensor and each reference measurement at each of the remaining temperature sensors of the array of temperature sensors; determine at least one threshold temperature based on the plurality of first temperature differences and the plurality of second temperature differences; determine that the first temperature measurement, one or more temperature measurements of the plurality of temperature measurements, or any combination thereof, satisfies the at least one threshold temperature; and in response to determining that the at least one threshold temperature is satisfied, generate the alert to the user.

Clause 23. The system of any of clauses 21 and 22, wherein the one or more processors are further programmed and/or configured to: determine that a temperature measurement of the plurality of temperature measurements at a most distant temperature sensor of the array of temperature sensors from the first temperature sensor satisfies a threshold temperature; and in response to determining that the temperature measurement of the most distant temperature sensor of the array of temperature sensors from the first temperature sensor satisfies the threshold temperature, generate the alert to the user, wherein the alert includes information associated with a potential peeling of the dressing and/or securement device.

Clause 24. The system of any of clauses 21-23, wherein the one or more processors are further programmed and/or configured to: determine that two or more temperature measurements of the first temperature measurement and the plurality of temperature measurements satisfy a threshold temperature; and in response to determining that the two or more temperature measurements of the first temperature measurement and the plurality of temperature measurements satisfy the threshold temperature, generate the alert to the user, wherein the alert includes information associated with a potential tunneling of the dressing and/or securement device.

Clause 25. The system of any of clauses 21-24, wherein the one or more processors are further programmed and/or configured to: determine that each temperature measurement of the first temperature measurement and the plurality of temperature measurements satisfies a threshold temperature; and in response to determining that each temperature measurement of the first temperature measurement and the plurality of temperature measurements satisfies the threshold temperature, generate the alert to the user, wherein the alert includes information associated with a potential removal of the dressing and/or securement device.

Clause 26. The system of any of clauses 21-25, wherein the dressing and/or securement device further includes a second temperature sensor, wherein the second temperature sensor is configured to obtain a second temperature measurement at a catheter tubing of the catheter, wherein the second temperature sensor is spaced apart from the first temperature sensor and the array of temperature sensors, and wherein the one or more processors are further programmed and/or configured to: determine that a first change over time in the second temperature satisfies an infusion temperature threshold; store a confirmation of an infusion operation in association with a record of the patient; determine a second change over time in the second temperature subsequent to the first change that satisfies a flush temperature threshold; and in response to determining that the second change over time in the second temperature satisfies the flush temperature threshold, generate the alert to the user, wherein the alert includes a prompt to the user to confirm delivery of a flushing fluid.

Clause 27. The system of any of clauses 21-26, wherein the one or more processors are further programmed and/or configured to: determine that at least one pattern of change in at least one of the following: the first temperature measurement, one or more temperature measurements of the plurality of temperature measurements, or any combination thereof, satisfies at least one threshold pattern of change; and in response to determining that the at least one pattern of change satisfies the at least one threshold pattern of change, generate the alert to the user, wherein the alert includes information associated with a potential issue with the dressing and/or securement device and/or the catheter.

Clause 28. The system of any of clauses 21-27, wherein the at least one pattern of change includes a change over time in one or more individual temperature measurements of the first temperature measurement and the plurality of temperature measurements.

Clause 29. The system of any of clauses 21-28, wherein the at least one pattern of change includes a change over time in a temperature difference between two or more temperature measurements of the first temperature measurement and the plurality of temperature measurements.

Clause 30. The system of any of clauses 21-29, wherein the one or more processors are further programmed and/or configured to: determine the at least one threshold pattern of change based on at least one of the following: a patient parameter associated with the patient, a medication parameter associated with a medication delivered, being delivered, or to be delivered to the patient, a care environment parameter associated with a care environment in which the patient is located, or any combination thereof.

Clause 31. The system of any of clauses 21-30, wherein, when the dressing and/or securement device is attached to the catheter and the body of the patient, the first temperature sensor and a closest temperature sensor of the array of temperature sensors to the first temperature sensor are located at a same distance from a catheter tubing of the catheter and a same distance from the catheter insertion site of the catheter on the body of the patient, and wherein the one or more processors are further programmed and/or configured to: determine that a change between the first temperature measurement and a temperature measurement of the plurality of temperature measurements at the closest temperature sensor of the array of temperature sensors to the first temperature sensor satisfies a threshold temperature; and in response to determining that the change between the first temperature measurement and the temperature measurement of the plurality of temperature measurements at the closest temperature sensor of the array of temperature sensors to the first temperature sensor satisfies the threshold temperature, generate, with at least one processor, the alert to the user, wherein the alert includes information associated with a potential issue with the dressing and/or securement device and/or the catheter.

Clause 32. The system of any of clauses 21-31, wherein the one or more processors are further programmed and/or configured to: determine at least one of (i) an increase in temperatures of temperature measurements from a most distant temperature sensor of the array of temperature sensors to the first temperature measurement and (ii) an increase in a temperature difference between the first temperature measurement and a temperature measurement at the most distant temperature sensor of the array of temperature sensors to the first temperature measurement that satisfies a threshold temperature increase; and in response to determining the at least one of (i) and (ii), with at least one processor, generate the alert to the user, wherein the alert includes information associated with a potential issue with the dressing and/or securement device and/or the catheter.

Clause 33. The system of any of clauses 21-32, wherein the dressing and/or securement device further includes a second temperature sensor, wherein the second temperature sensor is configured to obtain a second temperature measurement at a catheter tubing of the catheter, wherein the second temperature sensor is spaced apart from the first temperature sensor and the array of temperature sensors, and wherein the one or more processors are further programmed and/or configured to: determine that a decrease in temperature between the first temperature sensor and a most distant temperature sensor of the array of temperature sensors from the first temperature sensor satisfies a threshold temperature; in response to determining that the decrease in temperature satisfies the threshold temperature, determine that a comparison of the first temperature measurement and at least one of the following: (i) the second temperature measurement at a current time and at least one time prior to the current time and (ii) a temperature measurement of a temperature sensor of the array of temperature sensors more distant from the catheter insertion site than the first temperature sensor, satisfy at least one threshold temperature; and in response to determining that the at least one threshold temperature is satisfied, generate the alert to the user, wherein the alert includes information associated with a potential issue with the dressing and/or securement device and/or the catheter.

Clause 34. The system of any of clauses 21-33, wherein the first temperature measurement and the plurality of temperature measurements are obtained at a periodic rate, and wherein the one or more processors are further programmed and/or configured to: determine the periodic rate based on at least one of the following: a patient parameter associated with the patient, a medication parameter associated with a medication delivered, being delivered, or to be delivered to the patient, a care environment parameter associated with a care environment in which the patient is located, or any combination thereof.

Clause 35. The system of any of clauses 21-34, wherein the dressing and/or securement device further includes a plurality of arrays of temperature sensors, wherein the plurality of arrays of temperature sensors are configured to obtain the plurality of temperature measurements at the plurality of locations on the body of the patient, and wherein the plurality of arrays are spaced apart about dressing and/or securement device.

Clause 36. The system of any of clauses 21-35, wherein the plurality of arrays is spaced apart around a circumference of a circle defined within a plane of the dressing and/or securement device, and wherein temperature sensors associated with individual arrays of the plurality of arrays are spaced apart radially at a plurality of different distances from a center of the circle.

Clause 37. The system of any of clauses 21-36, wherein an array of the plurality of arrays includes the first temperature sensor.

Clause 38. The system of any of clauses 21-37, wherein the dressing and/or securement device includes a marking or opening indicating an orientation of the support member for attachment at the catheter insertion site of the catheter on the body of the patient.

Clause 39. The system of any of clauses 21-38, wherein the dressing and/or securement device includes a support member, wherein the support member includes the first temperature sensor and the plurality of temperature sensors, and wherein the support member further includes an adhesive layer.

Clause 40. The system of any of clauses 21-39, wherein the dressing and/or securement device includes an antimicrobial disk.

Clause 41. A dressing and/or securement device for a catheter, comprising: a support member including: a first temperature sensor configured to obtain a first temperature measurement at a first location on a body of a patient adjacent a catheter insertion site of the catheter; and an array of temperature sensors configured to obtain a plurality of temperature measurements at a plurality of locations on the body of the patient, wherein each temperature sensor of the array of temperature sensors is spaced apart from the first temperature sensor on the support member, and wherein the array of temperature sensors includes temperature sensors at a plurality of different distances from the first temperature sensor; and a wired or wireless communication device configured to communicate the first temperature measurement and the plurality of temperature measurements to one or more processors.

Clause 42. The dressing and/or securement device of clause 41, further comprising: the one or more processors, wherein the one or more processors are programmed and/or configured to: determine, based on the first temperature measurement and the plurality of temperature measurements, an alert condition associated with the dressing and/or securement device for the catheter and/or the catheter; and in response to determining the alert condition, generate an alert to a user.

Clause 43. The dressing and/or securement device of any of clauses 41 and 42, wherein the first temperature sensor is further configured to obtain a first reference measurement at the first location on the body of the patient, wherein the array of temperature sensors is further configured to obtain a plurality of reference measurements at the plurality of locations on the body of the patient, and wherein the one or more processors are further programmed and/or configured to: determine a plurality of first temperature differences between the first reference measurement and each of the plurality of reference measurements; determine a plurality of second temperature differences between a reference measurement at a most distant temperature sensor of the array of temperature sensors from the first temperature sensor and each reference measurement at each of the remaining temperature sensors of the array of temperature sensors; determine at least one threshold temperature based on the plurality of first temperature differences and the plurality of second temperature differences; determine that the first temperature measurement, one or more temperature measurements of the plurality of temperature measurements, or any combination thereof, satisfies the at least one threshold temperature; and in response to determining that the at least one threshold temperature is satisfied, generate the alert to the user.

Clause 44. The dressing and/or securement device of any of clauses 41-43, wherein the one or more processors are further programmed and/or configured to: determine that a temperature measurement of the plurality of temperature measurements at a most distant temperature sensor of the array of temperature sensors from the first temperature sensor satisfies a threshold temperature; and in response to determining that the temperature measurement of the most distant temperature sensor of the array of temperature sensors from the first temperature sensor satisfies the threshold temperature, generate the alert to the user, wherein the alert includes information associated with a potential peeling of the dressing and/or securement device.

Clause 45. The dressing and/or securement device of any of clauses 41-44, wherein the one or more processors are further programmed and/or configured to: determine that two or more temperature measurements of the first temperature measurement and the plurality of temperature measurements satisfy a threshold temperature; and in response to determining that the two or more temperature measurements of the first temperature measurement and the plurality of temperature measurements satisfy the threshold temperature, generate the alert to the user, wherein the alert includes information associated with a potential tunneling of the dressing and/or securement device.

Clause 46. The dressing and/or securement device of any of clauses 41-45, wherein the one or more processors are further programmed and/or configured to: determine that each temperature measurement of the first temperature measurement and the plurality of temperature measurements satisfies a threshold temperature; and in response to determining that each temperature measurement of the first temperature measurement and the plurality of temperature measurements satisfies the threshold temperature, generate the alert to the user, wherein the alert includes information associated with a potential removal of the dressing and/or securement device.

Clause 47. The dressing and/or securement device of any of clauses 41-46, wherein the support member further includes a second temperature sensor, wherein the second temperature sensor is configured to obtain a second temperature measurement at a catheter tubing of the catheter, wherein the second temperature sensor is spaced apart from the first temperature sensor and the array of temperature sensors on the support member, and wherein the one or more processors are further programmed and/or configured to: determine that a first change over time in the second temperature satisfies an infusion temperature threshold; store a confirmation of an infusion operation in association with a record of the patient; determine a second change over time in the second temperature subsequent to the first change that satisfies a flush temperature threshold; and in response to determining that the second change over time in the second temperature satisfies the flush temperature threshold, generate the alert to the user, wherein the alert includes a prompt to the user to confirm delivery of a flushing fluid.

Clause 48. The dressing and/or securement device of any of clauses 41-47, wherein the one or more processors are further programmed and/or configured to: determine that at least one pattern of change in at least one of the following: the first temperature measurement, one or more temperature measurements of the plurality of temperature measurements, or any combination thereof, satisfies at least one threshold pattern of change; and in response to determining that the at least one pattern of change satisfies the at least one threshold pattern of change, generate the alert to the user, wherein the alert includes information associated with a potential issue with the dressing and/or securement device and/or the catheter.

Clause 49. The dressing and/or securement device of any of clauses 41-48, wherein the at least one pattern of change includes a change over time in one or more individual temperature measurements of the first temperature measurement and the plurality of temperature measurements.

Clause 50. The dressing and/or securement device of any of clauses 41-49, wherein the at least one pattern of change includes a change over time in a temperature difference between two or more temperature measurements of the first temperature measurement and the plurality of temperature measurements.

Clause 51. The dressing and/or securement device of any of clauses 41-50, wherein the one or more processors are further programmed and/or configured to: determine the at least one threshold pattern of change based on at least one of the following: a patient parameter associated with the patient, a medication parameter associated with a medication delivered, being delivered, or to be delivered to the patient, a care environment parameter associated with a care environment in which the patient is located, or any combination thereof.

Clause 52. The dressing and/or securement device of any of clauses 41-51, wherein, when the dressing and/or securement device is attached to the catheter and the body of the patient, the first temperature sensor and a closest temperature sensor of the array of temperature sensors to the first temperature sensor are located at a same distance from a catheter tubing of the catheter and a same distance from the catheter insertion site of the catheter on the body of the patient, and wherein the one or more processors are further programmed and/or configured to: determine that a change between the first temperature measurement and a temperature measurement of the plurality of temperature measurements at the closest temperature sensor of the array of temperature sensors to the first temperature sensor satisfies a threshold temperature; and in response to determining that the change between the first temperature measurement and the temperature measurement of the plurality of temperature measurements at the closest temperature sensor of the array of temperature sensors to the first temperature sensor satisfies the threshold temperature, generate, with at least one processor, the alert to the user, wherein the alert includes information associated with a potential issue with the dressing and/or securement device and/or the catheter.

Clause 53. The dressing and/or securement device of any of clauses 41-52, wherein the one or more processors are further programmed and/or configured to: determine at least one of (i) an increase in temperatures of temperature measurements from a most distant temperature sensor of the array of temperature sensors to the first temperature measurement and (ii) an increase in a temperature difference between the first temperature measurement and a temperature measurement at the most distant temperature sensor of the array of temperature sensors to the first temperature measurement that satisfies a threshold temperature increase; and in response to determining the at least one of (i) and (ii), with at least one processor, generate the alert to the user, wherein the alert includes information associated with a potential issue with the dressing and/or securement device and/or the catheter.

Clause 54. The dressing and/or securement device of any of clauses 41-53, wherein the support member further includes a second temperature sensor, wherein the second temperature sensor is configured to obtain a second temperature measurement at a catheter tubing of the catheter, wherein the second temperature sensor is spaced apart from the first temperature sensor and the array of temperature sensors on the support member, and wherein the one or more processors are further programmed and/or configured to: determine that a decrease in temperature between the first temperature sensor and a most distant temperature sensor of the array of temperature sensors from the first temperature sensor satisfies a threshold temperature; in response to determining that the decrease in temperature satisfies the threshold temperature, determine that a comparison of the first temperature measurement and at least one of the following: (i) the second temperature measurement at a current time and at least one time prior to the current time and (ii) a temperature measurement of a temperature sensor of the array of temperature sensors more distant from the catheter insertion site than the first temperature sensor, satisfy at least one threshold temperature; and in response to determining that the at least one threshold temperature is satisfied, generate the alert to the user, wherein the alert includes information associated with a potential issue with the dressing and/or securement device and/or the catheter.

Clause 55. The dressing and/or securement device of any of clauses 41-54, wherein the first temperature measurement and the plurality of temperature measurements are obtained at a periodic rate, and wherein the one or more processors are further programmed and/or configured to: determine the periodic rate based on at least one of the following: a patient parameter associated with the patient, a medication parameter associated with a medication delivered, being delivered, or to be delivered to the patient, a care environment parameter associated with a care environment in which the patient is located, or any combination thereof.

Clause 56. The dressing and/or securement device of any of clauses 41-55, wherein the dressing and/or securement device further includes a plurality of arrays of temperature sensors, wherein the plurality of arrays of temperature sensors are configured to obtain the plurality of temperature measurements at the plurality of locations on the body of the patient, and wherein the plurality of arrays are spaced apart about the support member.

Clause 57. The dressing and/or securement device of any of clauses 41-57, wherein the plurality of arrays is spaced apart around a circumference of a circle defined within a plane of the support member, and wherein temperature sensors associated with individual arrays of the plurality of arrays are spaced apart radially at a plurality of different distances from a center of the circle.

Clause 58. The dressing and/or securement device of any of clauses 41-57, wherein an array of the plurality of arrays includes the first temperature sensor.

Clause 59. The dressing and/or securement device of any of clauses 41-58, wherein the dressing and/or securement device includes a marking or opening indicating an orientation of the support member for attachment at the catheter insertion site of the catheter on the body of the patient.

Clause 60. The dressing and/or securement device of any of clauses 41-59, wherein the support member includes the first temperature sensor and the plurality of temperature sensors, and wherein the support member further includes an adhesive layer.

Clause 61. The dressing and/or securement device of any of clauses 41-60, wherein support member includes an antimicrobial disk.

Clause 62. A computer program product comprising at least one non-transitory computer-readable medium including program instructions that, when executed by at least one processor, cause the at least one processor to: obtain a first temperature measurement associated with a first location on a body of a patient adjacent a catheter insertion site of a catheter on the body of the patient; obtain a plurality of temperature measurements associated with a plurality of locations on the body of the patient, wherein each of the plurality of locations is spaced apart from the first location, and wherein the plurality of locations includes locations at a plurality of different distances from the first location; determine, based on the first temperature measurement and the plurality of temperature measurements, an alert condition associated with the catheter and/or a dressing and/or securement device for the catheter; and in response to determining that the at least one threshold is satisfied, generate an alert to a user.

Clause 63. The computer program product of clause 62, wherein the instructions further cause the at least one processor to: obtain a first reference measurement associated with the first location on the body of the patient; obtain a plurality of reference measurements associated with the plurality of locations on the body of the patient; determine a plurality of first temperature differences between the first reference measurement and each of the plurality of reference measurements; determine a plurality of second temperature differences between a reference measurement at a most distant location of the plurality of locations from the first location and each reference measurement at each of the remaining locations of the plurality of locations; determine at least one threshold temperature based on the plurality of first temperature differences and the plurality of second temperature differences; determine that the first temperature measurement, one or more temperature measurements of the plurality of temperature measurements, or any combination thereof, satisfies the at least one threshold temperature; and in response to determining that the at least one threshold temperature is satisfied, generate the alert to the user.

Clause 64. The computer program product of any of clauses 62 and 63, wherein the instructions further cause the at least one processor to: determine that a temperature measurement of the plurality of temperature measurements at a most distant location of the plurality of locations from the first location satisfies a threshold temperature; and in response to determining that the temperature measurement at the most distant location of the plurality of locations from the first location satisfies the threshold temperature, generate the alert to the user, wherein the alert includes information associated with a potential peeling of the dressing and/or securement device.

Clause 65. The computer program product of any of clauses 62-64, wherein the instructions further cause the at least one processor to: determine that two or more temperature measurements of the first temperature measurement and the plurality of temperature measurements satisfy a threshold temperature; and in response to determining that the two or more temperature measurements of the first temperature measurement and the plurality of temperature measurements satisfy the threshold temperature, generate the alert to the user, wherein the alert includes information associated with a potential tunneling of the dressing and/or securement device.

Clause 66. The computer program product of any of clauses 62-65, wherein the instructions further cause the at least one processor to: determine that each temperature measurement of the first temperature measurement and the plurality of temperature measurements satisfies a threshold temperature; and in response to determining that each temperature measurement of the first temperature measurement and the plurality of temperature measurements satisfies the threshold temperature, generate the alert to the user, wherein the alert includes information associated with a potential removal of the dressing and/or securement device.

Clause 67. The computer program product of any of clauses 62-66, wherein the instructions further cause the at least one processor to: obtain a second temperature measurement associated with a catheter tubing of the catheter; determine that a first change over time in the second temperature satisfies an infusion temperature threshold; store a confirmation of an infusion operation in association with a record of the patient; determine a second change over time in the second temperature subsequent to the first change that satisfies a flush temperature threshold; and in response to determining that the second change over time in the second temperature satisfies the flush temperature threshold, generate the alert to the user, wherein the alert includes a prompt to the user to confirm delivery of a flushing fluid.

Clause 68. The computer program product of any of clauses 62-67, wherein the instructions further cause the at least one processor to: determine that at least one pattern of change in at least one of the following: the first temperature measurement, one or more temperature measurements of the plurality of temperature measurements, or any combination thereof, satisfies at least one threshold pattern of change; and in response to determining that the at least one pattern of change satisfies the at least one threshold pattern of change, generate the alert to the user, wherein the alert includes information associated with a potential issue with the dressing and/or securement device and/or the catheter.

Clause 69. The computer program product of any of clauses 62-68, wherein the at least one pattern of change includes a change over time in one or more individual temperature measurements of the first temperature measurement and the plurality of temperature measurements.

Clause 70. The computer program product of any of clauses 62-69, wherein the at least one pattern of change includes a change over time in a temperature difference between two or more temperature measurements of the first temperature measurement and the plurality of temperature measurements.

Clause 71. The computer program product of any of clauses 62-70, wherein the instructions further cause the at least one processor to: determine the at least one threshold pattern of change based on at least one of the following: a patient parameter associated with the patient, a medication parameter associated with a medication delivered, being delivered, or to be delivered to the patient, a care environment parameter associated with a care environment in which the patient is located, or any combination thereof.

Clause 72. The computer program product of any of clauses 62-71, wherein the first location and a closest location of the plurality of locations to the first location are located at a same distance from a catheter tubing of the catheter and a same distance from the catheter insertion site of the catheter on the body of the patient, and wherein the instructions further cause the at least one processor to: determine that a change between the first temperature measurement and a temperature measurement of the plurality of temperature measurements at the closest location of the plurality of locations to the first location satisfies a threshold temperature; and in response to determining that the change between the first temperature measurement and the temperature measurement of the plurality of temperature measurements at the closest location of the plurality of locations to the first location satisfies the threshold temperature, generate the alert to the user, wherein the alert includes information associated with a potential issue with the dressing and/or securement device and/or the catheter.

Clause 73. The computer program product of any of clauses 62-72, wherein the instructions further cause the at least one processor to: determine at least one of (i) an increase in temperatures of temperature measurements from a most distant location of the plurality of locations to the first temperature measurement and (ii) an increase in a temperature difference between the first temperature measurement and a temperature measurement at the most distant location of the plurality of locations to the first temperature measurement that satisfies a threshold temperature increase; and in response to determining the at least one of (i) and (ii), generate the alert to the user, wherein the alert includes information associated with a potential issue with the dressing and/or securement device and/or the catheter.

Clause 74. The computer program product of any of clauses 62-73, wherein the instructions further cause the at least one processor to: obtain a second temperature measurement associated with a catheter tubing of the catheter; determine, with at least one processor, that a decrease in temperature between the first location and a most distant location of the plurality of locations from the first location satisfies a threshold temperature; in response to determining that the decrease in temperature satisfies the threshold temperature, determine, with at least one processor, that a comparison of the first temperature measurement and at least one of the following: (i) the second temperature measurement at a current time and at least one time prior to the current time and (ii) a temperature measurement of a location of the plurality of locations more distant from the catheter insertion site than the first location, satisfy at least one threshold temperature; and in response to determining that the at least one threshold temperature is satisfied, generate, with at least one processor, the alert to the user, wherein the alert includes information associated with a potential issue with the dressing and/or securement device and/or the catheter.

Clause 75. The computer program product of any of clauses 62-74, wherein the first temperature measurement and the plurality of temperature measurements are obtained at a periodic rate, and wherein the instructions further cause the at least one processor to: determine the periodic rate based on at least one of the following: a patient parameter associated with the patient, a medication parameter associated with a medication delivered, being delivered, or to be delivered to the patient, a care environment parameter associated with a care environment in which the patient is located, or any combination thereof.

Clause 76. The computer program product of any of clauses 62-75, wherein the plurality of locations include a plurality of arrays spaced apart around a circumference of a circle surrounding the catheter insertion site, and wherein locations of the plurality of locations associated with individual arrays of the plurality of arrays are spaced apart radially at a plurality of different distances from the catheter insertion site.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of limits. As used in the specification and the claims, the singular form of "a," "an," and "the" include plural referents unless the context clearly dictates otherwise.

BRIEF DESCRIPTION OF THE DRAWINGS

Additional advantages and details of embodiments or aspects of the present disclosure are explained in greater detail below with reference to the exemplary embodiments that are illustrated in the accompanying schematic figures, in which:

FIG. 1B is a top view of non-limiting embodiments or aspects of components of one or more devices and/or one or more systems of FIG. 1A;

DETAILED DESCRIPTION

Figure 1A:
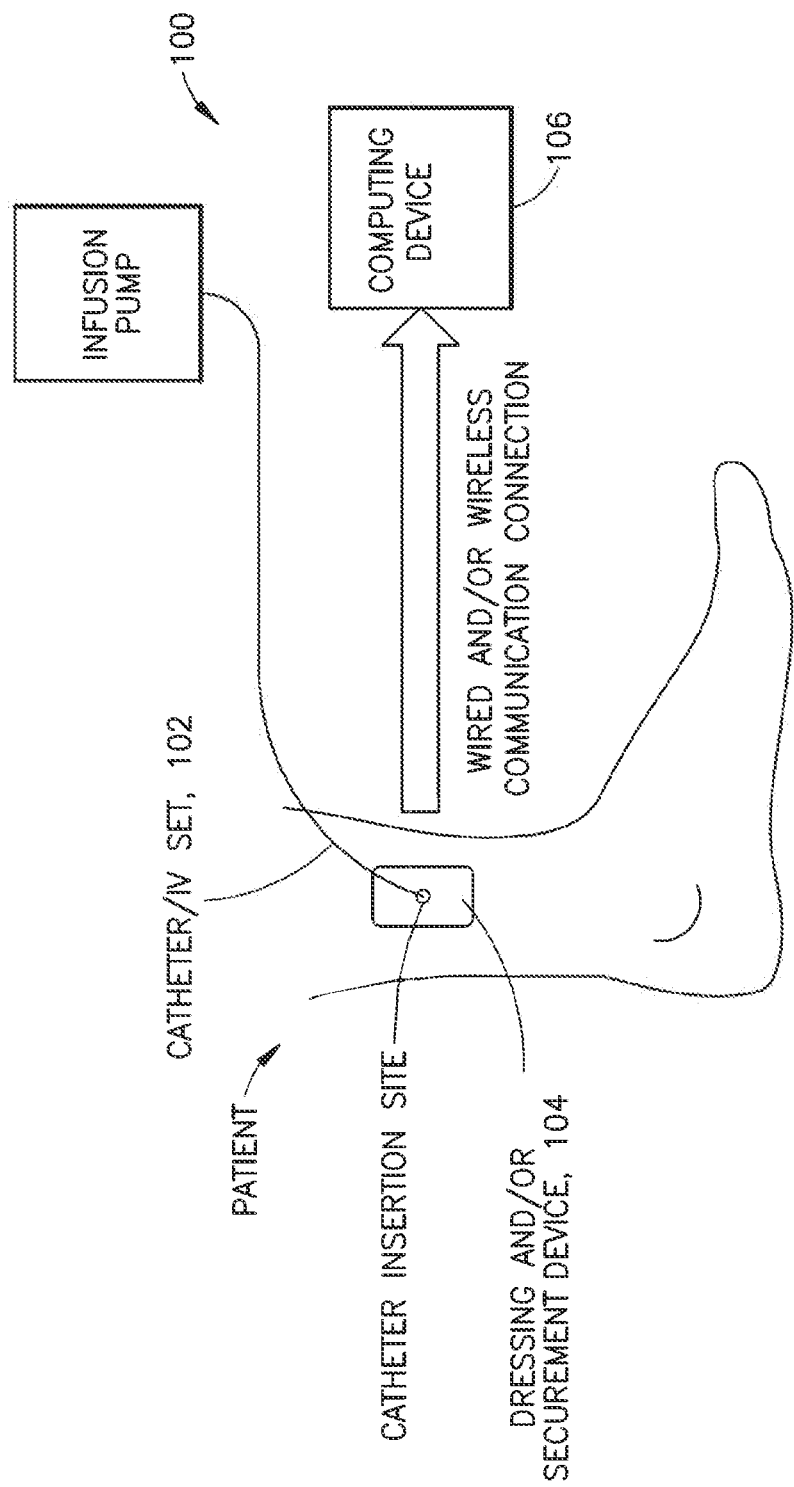
FIG. 1A is a diagram of non-limiting embodiments or aspects of an environment in which systems, devices, products, apparatus, and/or methods, described herein, may be implemented.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms "end," "upper," "lower," "right," "left," "vertical," "horizontal," "top," "bottom," "lateral," "longitudinal," and derivatives thereof shall relate to the present disclosure as it is oriented in the drawing figures. However, it is to be understood that the present disclosure may assume various alternative variations and step sequences, except where expressly specified to the contrary. It is also to be understood that the specific devices and processes illustrated in the attached drawings, and described in the following specification, are simply exemplary embodiments or aspects of the present disclosure. Hence, specific dimensions and other physical characteristics related to the embodiments or aspects of the embodiments disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least in partially on" unless explicitly stated otherwise.

As used herein, the terms "communication" and "communicate" refer to the receipt or transfer of one or more signals, messages, commands, or other type of data. For one unit (e.g., any device, system, or component thereof) to be in communication with another unit means that the one unit is able to directly or indirectly receive data from and/or transmit data to the other unit. This may refer to a direct or indirect connection that is wired and/or wireless in nature. Additionally, two units may be in communication with each other even though the data transmitted may be modified, processed, relayed, and/or routed between the first and second unit. For example, a first unit may be in communication with a second unit even though the first unit passively receives data and does not actively transmit data to the second unit. As another example, a first unit may be in communication with a second unit if an intermediary unit processes data from one unit and transmits processed data to the second unit. It will be appreciated that numerous other arrangements are possible.

It will be apparent that systems and/or methods, described herein, can be implemented in different forms of hardware, software, or a combination of hardware and software. The actual specialized control hardware or software code used to implement these systems and/or methods is not limiting of the implementations. Thus, the operation and behavior of the systems and/or methods are described herein without reference to specific software code, it being understood that software and hardware can be designed to implement the systems and/or methods based on the description herein.

As used herein, the term "computing device" or "computer device" may refer to one or more electronic devices that are configured to directly or indirectly communicate with or over one or more networks. The computing device may be a mobile device, a desktop computer, or the like. Furthermore, the term "computer" may refer to any computing device that includes the necessary components to receive, process, and output data, and normally includes a display, a processor, a memory, an input device, and a network interface. An "application" or "application program interface" (API) refers to computer code or other data stored on a computer-readable medium that may be executed by a processor to facilitate the interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, touchscreen, etc.).

As used herein, the term "server" may refer to or include one or more processors or computers, storage devices, or similar computer arrangements that are operated by or facilitate communication and processing for multiple parties in a network environment, such as the Internet, although it will be appreciated that communication may be facilitated over one or more public or private network environments and that various other arrangements are possible. Further, multiple computers, e.g., servers, or other computerized devices, such as POS devices, directly or indirectly communicating in the network environment may constitute a "system," such as a merchant's POS system. As used herein, the term "data center" may include one or more servers, or other computing devices, and/or databases.

As used herein, the term "mobile device" may refer to one or more portable electronic devices configured to communicate with one or more networks. As an example, a mobile device may include a cellular phone (e.g., a smartphone or standard cellular phone), a portable computer (e.g., a tablet computer, a laptop computer, etc.), a wearable device (e.g., a watch, pair of glasses, lens, clothing, and/or the like), a personal digital assistant (PDA), and/or other like devices. The terms "client device" and "user device," as used herein, refer to any electronic device that is configured to communicate with one or more servers or remote devices and/or systems. A client device or user device may include a mobile device, a network-enabled appliance (e.g., a network-enabled television, refrigerator, thermostat, and/or the like), a computer, and/or any other device or system capable of communicating with a network.

As used herein, the term "application" or "application program interface" (API) refers to computer code, a set of rules, or other data stored on a computer-readable medium that may be executed by a processor to facilitate interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, etc.).

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc. In some non-limiting embodiments or aspects, satisfying a threshold may refer to recognition of a pattern or trend in a signal or measurement as a result of a pattern recognition technique, a machine learning technique, a data mining technique, a slope of signal analysis, an Xbar R chart analysis, and/or the like being applied to the signal or measurement. For example, satisfying a threshold may be based on a dynamic time based analysis of at least one of the following: a signal or measurement, a plurality of signals or measurements, differences between the plurality of signals or measurements, or any combination thereof. As an example, a threshold may mean an amount of change and may not be represented by a single number, but by a more complex pattern of change, which may be determined based on machine learning and/or pattern recognition.

Non-limiting embodiments or aspects of the present disclosure provide systems, devices, products, apparatus, and/or methods that obtain, with a first temperature sensor of a dressing and/or securement device for a catheter, a first temperature measurement at a first location on a body of a patient adjacent a catheter insertion site of the catheter; obtain, with a second temperature sensor of the dressing and/or securement device, a second temperature measurement at a catheter tubing of the catheter; and/or obtain, with an array of temperature sensors of the dressing and/or securement device, a plurality of temperature measurements at a plurality of locations on the body of the patient, wherein each of the plurality of locations is spaced apart from the first location, and wherein the plurality of locations includes locations at a plurality of different distances from the first location. A processor determines, based on the first temperature measurement, the second temperature measurement, and/or the plurality of temperature measurements, an alert condition associated with the dressing and/or securement device and/or the catheter and, in response to determining the alert condition, generates an alert to a user.

In this way, more accurate temperature analysis of an intravenous catheter site that uses a control temperature measurement or reading to account for fluctuations in a patient's basal body temperature as well as a control temperature measurement or reading to account for temperature effects due to a fluid being infused through the catheter may be provided. Further, absolute and differential changes in temperature in a spatially relevant pattern and over time may be monitored, with a dressing and/or securement device oriented to ensure that the catheter tubing location is in a known orientation/position such that control temperature measurements or readings can be obtained for both the patient's skin at a location sufficiently distant from the catheter entry point, at a defined distance from or collocated with the patient's catheter infusion tubing (again sufficiently distant from the catheter entry point), and the catheter entry point, at the same distance from the patient's tubing as the control tubing. For example, alerts may be triggered based on changes in temperature over time (e.g., temporally, etc.)

and/or based on changes in temperature in a spatial pattern represented by a positioning or locations of temperature sensors (e.g. using one or more arrays of sensors arranged radially from the catheter insertion site, etc.). As an example, if heating (and/or cooling) progresses radially away from the catheter insertion site and/or in a broadening fashion (e.g., with the heated area expanded at a given circumference, etc.) an alert may be generated at a lower threshold as compared to alerts based on a single array or in a non-spread like pattern (e.g., which may potentially result from random variations more than real changes in temperature, etc.). Further, a reference temperature at an outer edge of a dressing and/or securement device (e.g., a temperature obtained at a location not adjacent to the catheter tubing and/or catheter insertion site, etc.) may be used to update threshold temperatures (e.g., as the catheter is in place for longer periods of time, the variability in this reference temperature reading may be used to ensure that "normal" variability at the site on a given patient does not trigger an alert, etc.).

Referring to FIG. 1A, non-limiting embodiments or aspects of an environment 100 in which systems, devices, products, apparatus, and/or methods, as described herein, may be implemented is shown. As shown in FIG. 1A, environment 100 may include catheter 102, dressing and/or securement device 104, and/or computing device 106.

Catheter 102 may include an IV catheter, a parenteral catheter, such as a urinary catheter, an anesthesia catheter, and/or the like, or any intra- or subdermal object which is superficial enough to elicit a surface temperature difference. Catheter 102 may be attached or connected to a patient at a catheter insertion site at which catheter 102 enters a body (e.g., the skin, etc.) of the patient. In some non-limiting embodiments or aspects, catheter 102 may be connected to an infusion pump as shown in FIG. 1A.

Figure 1C:
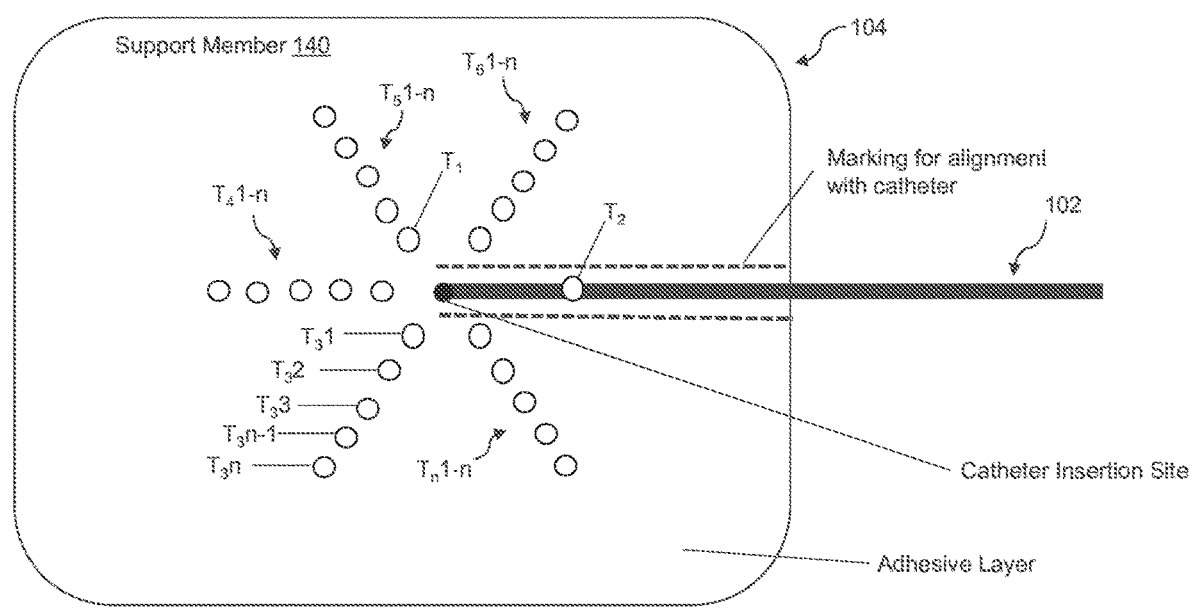
FIG. 1C is a schematic view of non-limiting embodiments or aspects of components of one or more devices and/or one or more systems of FIGS. 1A and 1B.
Figure 1D:
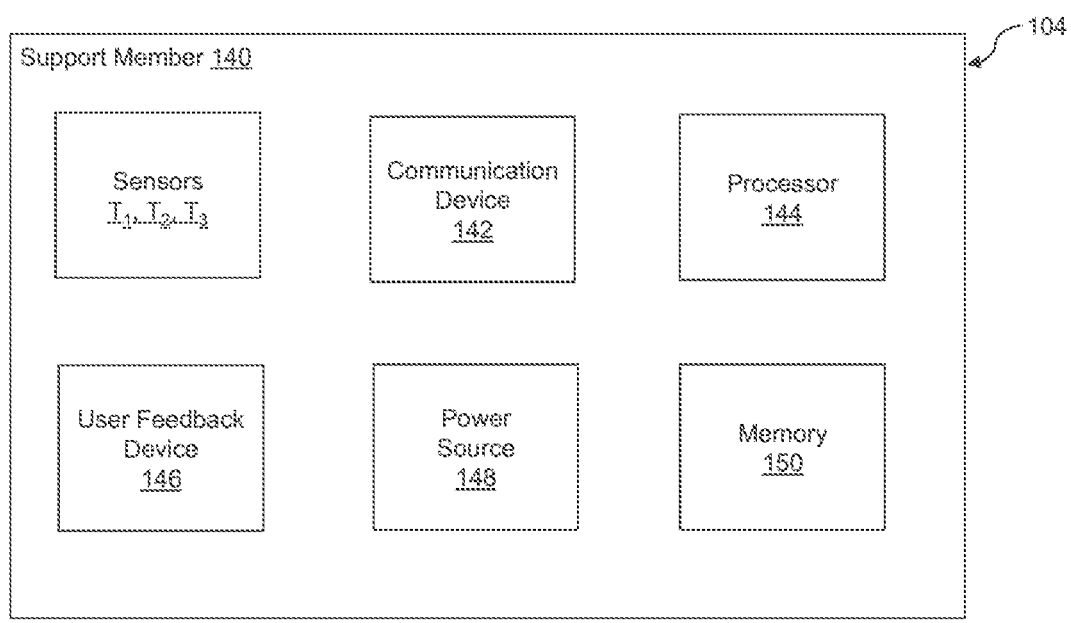
FIG. 1D is a block diagram of non-limiting embodiments or aspects of components of one or more devices and/or one or more systems of FIGS. 1A-1C.

Still referring to FIG. 1A, and also referring to FIGS. 1B-1D, dressing and/or securement device 104 may include support member 140, first temperature sensor $T_1$, second temperature sensor $T_2$, array of temperature sensors $T_3$ (e.g., temperature sensors $T_31$ through $T_3n$, etc.), and/or communication device 142. Although first temperature sensor $T_1$, second temperature sensor $T_2$, and array of temperature sensors $T_3$ are shown in FIGS. 1B and 1C as part of a same dressing and/or securement device 104, non-limiting embodiments or aspects are not limited thereto, and first temperature sensor $T_1$, second temperature sensor $T_2$, and array of temperature sensors $T_3$ may be included on a plurality of different dressing and/or securement devices and/or a plurality of different support members. For example, array of temperature sensors $T_3$ may be located at any location on a surface of a body of a patient and/or internal to the body of the patient, and/or second temperature sensor $T_2$ may be located over any portion of catheter 102. As an example, first temperature sensor $T_1$ may be located on a needle of catheter 102 (e.g. at a needle tip of catheter 102 within a body of a patient, etc.). However, it is noted that having first temperature sensor $T_1$, second temperature sensor $T_2$, and array of temperature sensors $T_3$ as part of a same catheter dressing and/or securement device may make applying the temperature sensors easier and/or faster. Further, body surface temperature can be highly variable across a body, as compared to core body temperature. For example, room temperature, blood circulation, circadian rhythm, systemic infection, clothing/bedding motion, and/or the like may make identifying true differences in temperature due to a catheter complication more complex. However, measuring a comparison temperature at or relatively near a catheter insertion site may eliminate much of this variability.

Support member 140 may include, carry, and/or house first temperature sensor $T_1$, second temperature sensor $T_2$, array of temperature sensors $T_3$, and/or communication device 142. In some non-limiting embodiments or aspects, support member 140 may be transparent. For example, dressing and/or securement device 104 may include a device from the BD StatLock® portfolio of devices. In some non-limiting embodiments or aspects, support member 140 includes a marking or opening indicating an orientation of the support member for attachment at a catheter insertion site of a catheter on a body of a patient. For example, the marking or opening may be aligned with the catheter insertion site of the catheter on the body of the patient when dressing and/or securement device 104 is applied to the catheter insertion site in contact with the catheter and/or the body of the patient. In some non-limiting embodiments or aspects, support member 140 includes an adhesive layer. For example, the adhesive layer may be used to attach dressing and/or securement device 104 to catheter 102 and/or the body of the patient.

First temperature sensor $T_1$ may be configured to obtain a first temperature measurement at a first location on a body of a patient adjacent a catheter insertion site of catheter 102 on the body of the patient. For example, first temperature sensor T1 may be located at a portion of support member 140 configured to be placed over and/or adjacent to the catheter insertion site (e.g., adjacent to a marking or opening indicating an orientation of the support member for attachment at the catheter insertion site, etc.).

Second temperature sensor $T_2$ may be configured to obtain a second temperature measurement at a catheter tubing of catheter 102. For example, second temperature sensor $T_2$ may be spaced apart from first temperature sensor $T_1$ and array of temperature sensors $T_3$ (e.g., spaced apart on support member 140 from first temperature sensor $T_1$ and array of temperature sensors $T_3$, etc.).

Array of temperature sensors $T_3$ may be configured to obtain a plurality of temperature measurements at a plurality of locations on the body of the patient. For example, each of the plurality of locations may be spaced apart from the first location, and the plurality of locations may include locations at a plurality of different distances from the first location. As an example, each temperature sensor of array of temperature sensors $T_3$ may be spaced apart from first temperature sensor $T_1$ and/or second temperature sensor $T_2$, and array of temperature sensors $T_3$ may include temperature sensors $T_31$ through $T_3n$ at a plurality of different distances from first temperature sensor $T_1$. In such an example, array of temperature sensors $T_3$ may extend toward an edge of support member 140 from an interior thereof with temperature sensor $T_31$ of the array located most distant from the edge (e.g., closest to a catheter insertion site, etc.) and temperature sensor $T_3n$ of the array located closest to the edge (e.g., most distant from the catheter insertion site, etc.).

In some non-limiting embodiments or aspects, array of temperature sensors $T_3$ may include a plurality of arrays of temperature sensors $T_3$. For example, as shown in FIG. 1C, a plurality of arrays of temperature sensors $T_31$-$n$, $T_41$-$n$, $T_51$-$n$, $T_61$-$n$, . . . $T_n1$-$n$ may be configured to obtain the plurality of temperature measurements at the plurality of locations on the body of the patient, and the plurality of arrays of temperature sensors $T_31$-$n$, $T_41$-$n$, $T_51$-$n$, $T_61$-$n$, . . . $T_n1$-$n$ may be spaced apart about dressing and/or securement device 104 (e.g., about support member 140, etc.). As an example, the plurality of arrays of temperature sensors $T_31$-$n$, $T_41$-$n$, $T_51$-$n$, $T_61$-$n$, ... $T_n1$-$n$ may be spaced apart around a circumference of a circle defined within a plane of dressing and/or securement device 104 (e.g., within a plane of support member 140, etc.), for example, spaced apart about a circumference of a circle surrounding and centered at the catheter insertion site, and temperature sensors $T_n1$-$n$ associated with individual arrays of the plurality of arrays may be spaced apart radially at a plurality of different distances from a center of the circle. For example, temperature sensors $T_n1$-$n$ associated with individual arrays of the plurality of arrays may extend toward an edge of support member 140 from an interior thereof with temperature sensor $T_n1$ of the array located most distant from the edge (e.g., closest to a catheter insertion site, etc.) and temperature sensor $T_nn$ of the array located closest to the edge (e.g., most distant from the catheter insertion site, etc.). In such an example, corresponding temperature sensors (e.g., $T_32$, $T_42$, $T_52$, $T_62$, ... $T_n2$, etc.) from different arrays of the plurality of arrays of temperature sensors $T_31$-$n$, $T_41$-$n$, $T_51$-$n$, $T_61$-$n$, ... $T_n1$-$n$ may be located at a same distance (e.g., at a same radius) from a catheter insertion site, first temperature sensor T1, second temperature sensor $T_2$, and/or a marking or opening indicating an orientation of the support member for attachment at the catheter insertion site. In some non-limiting embodiments or aspects, an array of the plurality of arrays $T_31$-$n$, $T_41$-$n$, $T_51$-$n$, $T_61$-$n$, ... $T_n1$-$n$ may include first temperature sensor $T_1$ (e.g., array $T_5$ as shown in FIG. 1C, etc.).

A temperature sensor may be configured to obtain a continuous temperature measurement (e.g., a continuous temperature signal over time, etc.) or to obtain a periodic temperature measurement (e.g., an instantaneous temperature measurement at intervals over a period of time, etc.). For example, a periodic temperature measurement may reduce an energy consumption of a temperature sensor. In some non-limiting embodiments or aspects, a periodic rate at which a temperature sensor obtains or measures a temperature measurement may be determined based on at least one of the following: a patient parameter associated with the patient (e.g., age, height, weight, patient history, such as a history of phlebitis, a history of dislodgment or other IV complications, a risk of complications associated with toddlers, babies, those with mental illness, and/or the like, etc.), a medication parameter associated with a medication delivered, being delivered, or to be delivered to the patient (e.g., medication type, vesicant type, dose, etc.), a care environment parameter associated with a care environment in which the patient is located (e.g., an area in which patient care occurs, such as a ward in a hospital, a hospital system, a hospital, an outpatient center, an elderly care center, a home care, or any other care area or building or space, and/or the like, etc.), or any combination thereof. As an example, a temperature sensor may be configured to obtain or measure a temperature measurement at a higher rate based on a patient parameter associated with a higher risk of complications (e.g., history of phlebitis and/or catheter dislodgement, a baby, etc.), a medication parameter associated with a higher risk of complications (e.g., vesicants, etc.), and/or a care environment associated with a higher risk of compilations (e.g., an emergency room, etc.).

In some non-limiting embodiments or aspects, a temperature sensor may include a Texas Instruments LMT70, LMT70A±0.05° C. Precision Analog Temperature Sensor and RTD and Precision NTC Thermistor IC. In some non-limiting embodiments or aspects, a temperature sensor may additionally, or alternatively, measure heat loss as a temperature measurement. For example, a temperature measurement including a heat loss measurement may be employed for measuring a temperature deeper in underlying tissue of a body of patient. In some non-limiting embodiments or aspects, a temperate sensor may include an optical sensor and/or illuminator configured to optically capture the temperature of the body of a patient on a color scale.

A temperature sensor may be attached to support member 140 via an adhesive, and/or a temperature sensor may be integrated with support member 140 and/or molded directly in support member 140. For example, a temperature sensor may be located on support member 140 at or adjacent to a surface of support member 140 that contacts the skin of a patient when dressing and/or securement device 104 is attached to the patient (e.g., at or adjacent to an adhesive layer of support member 140, etc.). In some non-limiting embodiments or aspects, a feature and/or an extension of dressing and/or securement device 104 may house a temperature sensor over and/or adjacent to a catheter insertion site on the body of the patient.

Electric connections to a temperature sensor may be formed or made via wires and/or conductive paths (e.g., formed via metallization (e.g., vapor deposition), conductive inks, polymers, etc.) on or through a material of support member 140. The electric connections may connect a temperature sensor to analog and/or digital electronics elsewhere on support member 140 and/or in computing device 106 as described herein in more detail. Components and/or electronics of dressing and/or securement device 104 may be located on and/or in support member 140 in a manner that reduces or minimizes obstruction of view through support member 140 and/or increases or optimizes a physical geometry of dressing and/or securement device 104 for a clinical environment.

Figure 1E:
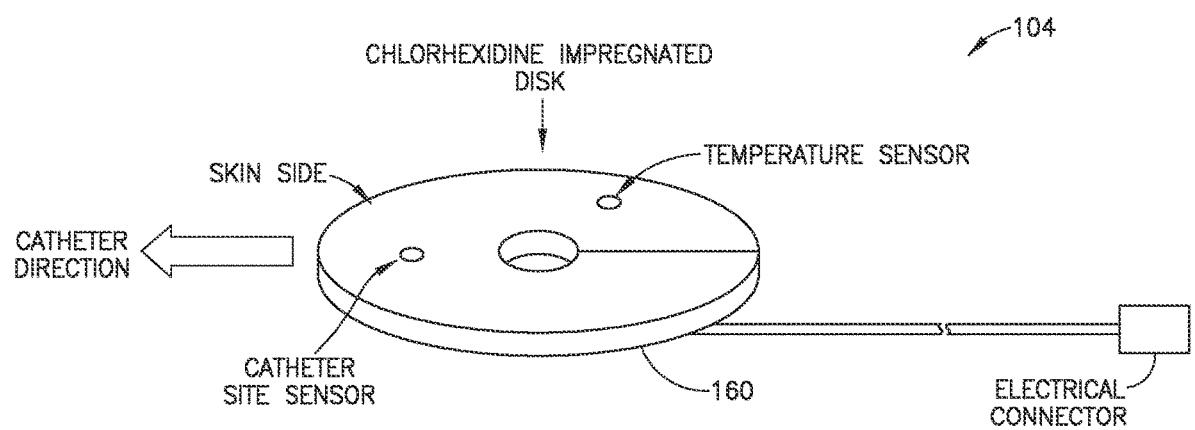
FIG. 1E is a perspective view of non-limiting embodiments or aspects of components of one or more devices and/or one or more systems of FIGS. 1A-1D.

In some non-limiting embodiments or aspects, dressing and/or securement device 104 may include antimicrobial disc 160, for example, as shown in FIG. 1E. For example, antimicrobial disc 160 may include first temperature sensor $T_1$, second temperature sensor $T_2$, array of temperature sensors $T_3$, and/or communication device 142. As an example, antimicrobial disc 160 may be placed over a catheter insertion site in contact with a body of a patient, and under support member 140 of dressing and/or securement device 104.

In some non-limiting embodiments or aspects, antimicrobial disc 160 includes and/or is formed entirely of an antimicrobial substance (e.g. a dried, freeze dried, and/or polymerized antimicrobial substance, an antimicrobial substance embedded in a polymer that releases the antimicrobial substance over time through elution, degradation of the polymer, and/or a mechanism to expel the antimicrobial substance over time upon a trigger, etc.). For example, swelling of a catheter insertion site may result in pressure applied to a chamber of antimicrobial disc 160 holding the antimicrobial substance, thereby resulting in release of the antimicrobial substance. As an example, fluid released from a wound at a catheter insertion site may result in swelling of a polymer of antimicrobial disc 160, thereby inducing release of the antimicrobial substance (e.g. by increasing a pore size of the polymer, by squeezing a chamber in which the antimicrobial substance is encapsulated, etc.). For example, localized heat at a catheter insertion site (e.g. due to an infection, etc.) may result in increased degradation of a polymer housing the antimicrobial substance to spur release of the antimicrobial substance from the polymer. In some non-limiting embodiments or aspects, antimicrobial disc 160 may serve to further help orient dressing and/or securement device 104 by serving as a visible target to be oriented directly over a catheter insertion site.

Communication device 142 may interconnect with computing device 106 (e.g., establish a connection to communicate) via wired connections, wireless connections, or a combination of wired and wireless connections. For example, communication device 142 may be configured to communicate information and/or data obtained by first temperature sensor $T_1$, second temperature sensor $T_2$, and/or array of temperature sensors $T_3$ to computing device 106. In some non-limiting embodiments or aspects, communication device 142 includes a wired communication device, such as one or more cables or wires directly connecting first temperature sensor $T_1$, second temperature sensor $T_2$, and/or array of temperature sensors $T_3$ to computing device 106 and/or one or more cables or wires directly connecting one or more computing devices or chips, which are connected to first temperature sensor $T_1$, second temperature sensor $T_2$, and/or array of temperature sensors $T_3$, to computing device 106. In some non-limiting embodiments or aspects, communication device 142 includes a wireless communication device including one or more computing devices, chips, contactless transmitters, contactless transceivers, NFC transmitters, RFID transmitters, contact based transmitters, Bluetooth Transceivers® and/or the like that enables communication device 142 to receive information directly from and/or communicate information directly to computing device 106 via a short (and/or long) range wireless communication connection (e.g., a communication connection that uses NFC protocol, a communication connection that uses Radio-frequency identification (RFID), a communication connection that uses a Bluetooth® wireless technology standard, a communication connection that uses a Wi-Fi wireless technology standard, a communication connection that uses a ZigBee® wireless technology standard, a communication connection that uses a LoRa wireless technology standard, and/or the like).

As shown in FIG. 1D, in some non-limiting embodiments or aspects, dressing and/or securement device 104 may include processor 144, user feedback device 146, power source 148, and/or memory 150. However, non-limiting embodiments or aspects are not limited thereto, and in some non-limiting embodiments or aspects, dressing and/or securement device 104 may include first temperature sensor $T_1$, second temperature sensor $T_2$, array of temperature sensors $T_3$, and/or communication device 142 in wired and/or wireless communication with an external and/or remote processor 144, external and/or remote user feedback device 146, external and/or remote power source 148, and/or an external and/or remote memory 150, such as computing device 106, and/or the like.

Processor 144 may be programmed and/or configured to determine, based on signals or sensor data (e.g., temperature measurements, etc.) received from first temperature sensor $T_1$, second temperature sensor $T_2$, and/or array of temperature sensors $T_3$, information and/or data associated with a condition associated with catheter 102 and/or dressing and/or securement device 104 (e.g., an alert condition, etc.). For example, processor 144 may be programmed and/or configured to determine based on signals or sensor data (e.g., temperature measurements, etc.) received from first temperature sensor $T_1$, second temperature sensor $T_2$, and/or array of temperature sensors $T_3$, an alert condition associated with dressing and/or securement device 104 and/or catheter 102. In such an example, processor 144 may determine an alert condition based on one or more thresholds as described in more detail herein. For example, processor 144 may compare signals or sensor data (e.g., temperature measurements, etc.) received from first temperature sensor $T_1$, second temperature sensor $T_2$, and/or array of temperature sensors $T_3$ to the one or more thresholds and, in response to a threshold of the one or more thresholds being satisfied, generate an alert condition associated with that threshold. In some non-limiting embodiments or aspects, processor 144 may include a low power microcontroller unit (MCU).

User feedback device 146 may be configured to provide, to a user, information and/or data associated with signals and/or sensor data (e.g., temperature measurements, etc.) received from first temperature sensor $T_1$, second temperature sensor $T_2$, and/or array of temperature sensors $T_3$ and/or processed by processor 144 (e.g., information and/or data associated with temperature measurements, differences in temperature measurements, trends or patterns in temperature measurements, etc.) and/or an indication and/or an alert associated with a condition of catheter 102 and/or dressing and/or securement device 104. For example, user feedback device 146 may include at least one of the following: a display, a light-emitting diode (LED), an audio output device (e.g., a buzzer, a speaker, etc.), or any combination thereof.

Power source 148 may be configured to power first temperature sensor $T_1$, second temperature sensor $T_2$, array of temperature sensors $T_3$, communication device 142, processor 144, user feedback device 146, and/or memory 150. For example, power source 148 may include a battery (e.g., a rechargeable battery, a disposable battery, etc.) and/or a connection to an external power source (e.g., computing device 106, an infusion pump, etc.).

Memory 150 may be configured to store information associated with signals and/or sensor data (e.g., temperature measurements, etc.) received from first temperature sensor $T_1$, second temperature sensor $T_2$, and/or array of temperature sensors $T_3$, information and/or data associated with a condition associated with catheter 102 and/or dressing and/or securement device 104 (e.g., an alert condition, etc.), patient data/parameters, medication data/parameters, care environment data/parameters, and/or data associated with a catheter and/or catheter insertion site location on a body of a patient. In some non-limiting embodiments or aspects, memory 150 may store calibration data associated with one or more calibration settings, one or more reference temperature settings, one or more temperature thresholds, or any combination thereof.

Computing device 106 may include one or more devices capable of receiving information and/or data from dressing and/or securement device 104 and/or communicating information and/or data to dressing and/or securement device 104. For example, computing device 106 may include a computing device, a server, a group of servers, a mobile device, a group of mobile devices, and/or the like. In some non-limiting embodiments or aspects, computing device 106 is connected via a wired connection, such as one or more cables or wires directly connecting computing device 106 to first temperature sensor $T_1$, second temperature sensor $T_2$, and/or array of temperature sensors $T_3$ and/or one or more cables or wires directly connecting computing device 106 to one or more computing devices or chips of dressing and/or securement device 104, which are connected to first temperature sensor $T_1$, second temperature sensor $T_2$, and/or array of temperature sensors $T_3$. In some non-limiting embodiments or aspects, computing device 106 includes one or more computing devices, chips, contactless transmitters, contactless transceivers, NFC transmitters, RFID transmitters, contact based transmitters, and/or the like that enables computing device 106 to receive information directly from and/or communicate information directly to communication device 142 via a short (and/or long) range wireless communication connection (e.g., a communication connection that uses NFC protocol, a communication connection that uses Radio-frequency identification (RFID), a communication connection that uses a Bluetooth® wireless technology standard, a communication connection that uses a Wi-Fi wireless technology standard, a communication connection that uses a ZigBee® wireless technology standard, a communication connection that uses a LoRa wireless technology standard, and/or the like). In some non-limiting embodiments or aspects, computing device 106 may include a reader box for an infusion pump and/or the infusion pump itself. In some non-limiting embodiments or aspects, computing device 106 may include and/or upload information and/or data to an electronic data management system, such as a hospital record system, a system used during a clinical trial to collect the trial related information, and/or the like.

The number and arrangement of devices and systems shown in FIGS. 1A-1E is provided as an example. There may be additional devices and/or systems, fewer devices and/or systems, different devices and/or systems, or differently arranged devices and/or systems than those shown in FIGS. 1A-1E. Furthermore, two or more devices and/or systems shown in FIGS. 1A-1E may be implemented within a single device and/or system, or a single device and/or system shown in FIGS. 1A-1E may be implemented as multiple, distributed devices and/or systems. Additionally, or alternatively, a set of devices and/or systems (e.g., one or more devices or systems) of environment 100 may perform one or more functions described as being performed by another set of devices and/or systems of environment 100.

Figure 2:
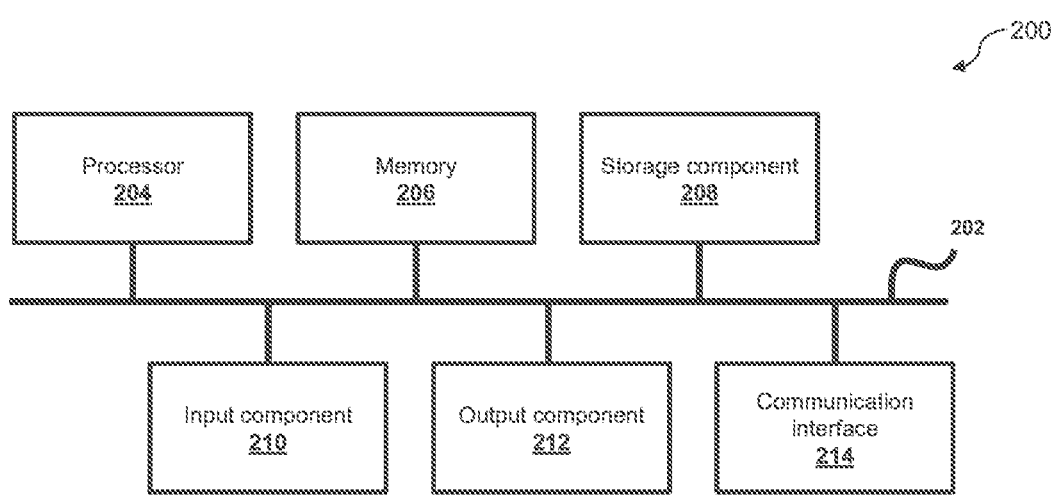
FIG. 2 is a block diagram of non-limiting embodiments or aspects of components of one or more devices and/or one or more systems of FIGS. 1A-1E.

Referring now to FIG. 2, FIG. 2 is a diagram of example components of a device 200. Device 200 may correspond to one or more devices of dressing and/or securement device 104 and/or one or more devices of computing device 106. In some non-limiting embodiments or aspects, one or more devices of dressing and/or securement device 104 and/or one or more devices of computing device 106 can include at least one device 200 and/or at least one component of device 200. As shown in FIG. 2, device 200 may include a bus 202, a processor 204, memory 206, a storage component 208, an input component 210, an output component 212, and a communication interface 214.

Bus 202 may include a component that permits communication among the components of device 200. In some non-limiting embodiments or aspects, processor 204 may be implemented in hardware, firmware, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 may include random access memory (RAM), read only memory (ROM), and/or another type of dynamic or static storage device (e.g., flash memory, magnetic memory, optical memory, etc.) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touch screen display, a keyboard, a keypad, a mouse, a button, a switch, a microphone, etc.). Additionally, or alternatively, input component 210 may include a sensor for sensing information (e.g., a global positioning system (GPS) component, an accelerometer, a gyroscope, an actuator, etc.). Output component 212 may include a component that provides output information from device 200 (e.g., a display, a speaker, one or more light-emitting diodes (LEDs), etc.).

Communication interface 214 may include a transceiver-like component (e.g., a transceiver, a separate receiver and transmitter, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally, or alternatively, hardwired circuitry may be used in place of or in combination with software instructions to perform one or more processes described herein. Thus, embodiments or aspects described herein are not limited to any specific combination of hardware circuitry and software.

Memory 206 and/or storage component 208 may include data storage or one or more data structures (e.g., a database, etc.). Device 200 may be capable of receiving information from, storing information in, communicating information to, or searching information stored in the data storage or one or more data structures in memory 206 and/or storage component 208.

The number and arrangement of components shown in FIG. 2 are provided as an example. In some non-limiting embodiments or aspects, device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

Figure 3:
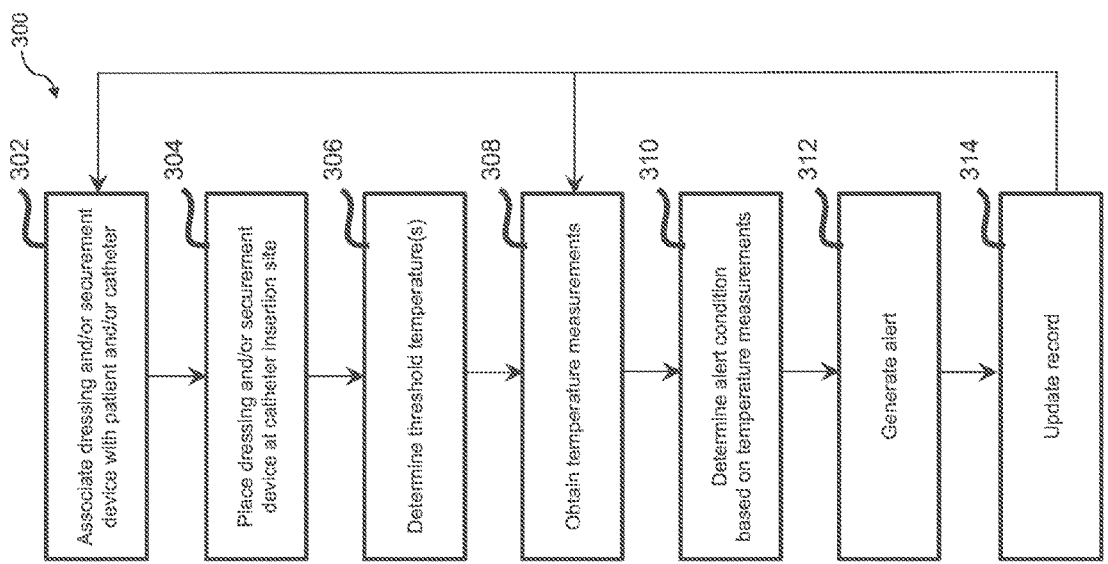
FIG. 3 is a flowchart of non-limiting embodiments or aspects of a process for temperature sensing for intravenous site condition detection.

Referring now to FIG. 3, FIG. 3 is a flowchart of non-limiting embodiments or aspects of a process 300 for intravenous site condition detection. In some non-limiting embodiments or aspects, one or more of the steps of process 300 may be performed (e.g., completely, partially, etc.) by dressing and/or securement device 104. In some non-limiting embodiments or aspects, one or more of the steps of process 300 may be performed (e.g., completely, partially, etc.) by another device or a group of devices separate from or including dressing and/or securement device 104, such as computing device 106 (e.g., one or more devices of computing device 106).

As shown in FIG. 3, at step 302, process 300 includes associating a dressing and/or securement device with a patient and/or a catheter/catheter insertion site. For example, computing system 106 may receive a unique identifier associated with dressing and/or securement device 104 and store the unique identifier in a database in association with a unique identifier of a patient and/or a unique identifier of catheter 102 and/or a catheter insertion site location of catheter 102 on a body of the patient. As an example, a clinician may scan a barcode, RFID tag, and/or the like on dressing and/or securement device 104 or, dressing and/or securement device 104 may automatically, upon opening a package containing dressing and/or securement device 104, transmit a signal to a nearest compatible electronic interface (e.g., computing system 106, etc.) to associate itself with the patient. The clinician may scan or manually enter a catheter/catheter insertion site of the patient to be associated with dressing and/or securement device 104.

As shown in FIG. 3, at step 304, process 300 includes placing a dressing and/or securement device at a catheter insertion site of a catheter for a patient. For example, a clinician may place dressing and/or securement device 104 over a catheter insertion site with a marking or opening indicating an orientation of support member 140 of dressing and/or securement device 104 for attachment at the catheter insertion site of catheter 102 on the body of the patient aligned with the catheter insertion site of catheter 102 on the body of the patient. As an example, a clinician may place dressing and/or securement device 104 over a catheter insertion site such that (i) first temperature sensor $T_1$ is located at and/or over a first location on the body of the patient adjacent the catheter insertion site of catheter 102, (ii) second temperature sensor $T_2$ is located at and/or over a catheter tubing of catheter 102, and (iii) array of temperature sensors $T_3 1-n$ is located at a plurality of locations on the body of the patient, wherein each of the plurality of locations is spaced apart from the first location, and wherein the plurality of locations includes locations at a plurality of different distances from the first location.

As shown in FIG. 3, at step 306, process 300 includes determining at least one threshold temperature. For example, dressing and/or securement device 104 (e.g., processor 144, etc.) and/or computing system 106 may determine at least one threshold temperature. For example, as described in more detail herein below with respect to step 310, dressing and/or securement device 104 (e.g., processor 144, etc.) and/or computing system 106 may compare signals or sensor data (e.g., temperature measurements, etc.) received from first temperature sensor $T_1$, second temperature sensor $T_2$, and/or array of temperature sensors $T_3$ to the at least one threshold temperature and, in response to a threshold temperature of the at least one threshold temperature being satisfied, generate an alert condition associated with that threshold temperature.

In some non-limiting embodiments or aspects, dressing and/or securement device 104 (e.g., processor 144, etc.) and/or computing system 106 may determine the at least one threshold temperature based on at least one of the following: a patient parameter associated with the patient (e.g., age, height, weight, patient history, such as a history of phlebitis, a history of dislodgment or other IV complications, a risk of complications associated with toddlers, babies, those with mental illness, and/or the like, etc.), a medication parameter associated with a medication delivered, being delivered, or to be delivered to the patient (e.g., medication type, vesicant type, dose, etc.), a care environment parameter associated with a care environment in which the patient is located (e.g., an area in which patient care occurs, such as a ward in a hospital, a hospital system, a hospital, an outpatient center, an elderly care center, a home care, or any other care area or building or space, and/or the like, etc.), or any combination thereof. For example, a threshold may be determined or set such that the threshold is more easily satisfied (e.g., satisfied by a lower value and/or amount of change, etc.) based on a patient parameter associated with a higher risk of complications (e.g., a history of phlebitis and/or catheter dislodgement, a baby, etc.), a medication parameter associated with a higher risk of complications (e.g., vesicants, etc.), and/or a care environment associated with a higher risk of complications (e.g., an emergency room, etc.). In some non-limiting embodiments or aspects, a threshold for an absolute temperature difference may be dependent on limits of the temperature sensors used to obtain the temperature measurements for determining the absolute temperature difference.

In some non-limiting embodiments or aspects, dressing and/or securement device 104 (e.g., processor 144, etc.) and/or computing system 106 may determine the at least one threshold temperature based on one or more reference measurements obtained by first temperature sensor $T_1$, second temperature sensor $T_2$, and/or array of temperature sensors $T_3$. For example, first temperature sensor $T_1$ may obtain a first reference measurement at the first location on the body of the patient and array of temperature sensors $T_3$ may obtain a plurality of reference measurements at the plurality of locations on the body of the patient. As an example, dressing and/or securement device 104 (e.g., processor 144, etc.) and/or computing system 106 may determine a plurality of first temperature differences between the first reference measurement and each of the plurality of reference measurements (e.g., a plurality of temperature differences between $T_1$ and $T_3 1$ through $T_3 n$, etc.), determine a plurality of second temperature differences between a reference measurement at a most distant location of the plurality of locations from the first location and each reference measurement at each of the remaining locations of the plurality of locations (e.g., a plurality of temperature differences between $T_3 n$ and $T_3 1$ through $T_3 n-1$, etc.), and determine at least one threshold temperature based on the plurality of first temperature differences and the plurality of second temperature differences. In such an example, dressing and/or securement device 104 (e.g., processor 144, etc.) and/or computing system 106 may determine the at least one threshold temperature to provide a baseline for understanding a variability of a body temperature of the patient to create a threshold for temperature variation as Threshold Variation=Multiplier X Average Temperature Variation, wherein the Multiplier may be automatically set and/or predetermined or set by a clinician/hospital, etc. (e.g., the Multiplier may be a fraction, such as 0.25, 0.5, and/or the like, a whole number, such as 1, 2, and/or the like, etc.).

In some non-limiting embodiments or aspects, dressing and/or securement device 104 (e.g., processor 144, etc.)

and/or computing system 106 may determine at least one threshold temperature as at least one predetermined threshold temperature.

As shown in FIG. 3, at step 308, process 300 includes obtaining temperature measurements. For example, first temperature sensor $T_1$ may obtain a first temperature measurement at a first location on a body of a patient adjacent a catheter insertion site of catheter 102 on the body of the patient, second temperature sensor $T_2$ may obtain a second temperature measurement at a catheter tubing of catheter 102, and/or array of temperature sensors $T_3$ (and/or $T_4$ through $T_n$, etc.) may obtain a plurality of temperature measurements at a plurality of locations on the body of the patient. In such an example, each of the plurality of locations may be spaced apart from the first location, and the plurality of locations may include locations at a plurality of different distances from the first location.

As shown in FIG. 3, at step 310, process 300 includes determining, based on temperature measurements, an alert condition. For example, dressing and/or securement device 104 (e.g., processor 144, etc.) and/or computing system 106 may determine, based on the first temperature measurement (e.g., at $T_1$, etc.), the second temperature measurement (e.g., at $T_2$, etc.), and/or the plurality of temperature measurements (e.g., at $T_3$, at $T_n$, etc.), an alert condition associated with dressing and/or securement device 104 and/or catheter 102. As an example, dressing and/or securement device 104 (e.g., processor 144, etc.) and/or computing system 106 may determine that the first temperature measurement, the second temperature measurement, one or more temperature measurements of the plurality of temperature measurements, or any combination thereof, satisfies at least one threshold temperature.

In some non-limiting embodiments or aspects, dressing and/or securement device 104 (e.g., processor 144, etc.) and/or computing system 106 may monitor the first temperature measurement (e.g., at $T_1$, etc.), the second temperature measurement (e.g., at $T_2$, etc.), and/or the plurality of temperature measurements (e.g., at $T_3$, at $T_n$, etc.) for patterns (e.g., absolute temperature change patterns, temporal temperature change patterns, spatial temperature change patterns between different temperature sensors, etc.) that satisfy at least one threshold pattern of change. As an example, dressing and/or securement device 104 (e.g., processor 144, etc.) and/or computing system 106 may determine that at least one pattern of change in at least one of the following: the first temperature measurement, the second temperature measurement, one or more temperature measurements of the plurality of temperature measurements, or any combination thereof, satisfies at least one threshold pattern of change. In such an example, the at least one pattern of change may include a change over time in one or more individual temperature measurements of the first temperature measurement and the plurality of temperature measurements and/or a change over time in a temperature difference between two or more temperature measurements of the first temperature measurement and the plurality of temperature measurements.

In some non-limiting embodiments or aspects, dressing and/or securement device 104 (e.g., processor 144, etc.) and/or computing system 106 may use pattern matching techniques and/or machine learning techniques to identify patterns or trends of concern (e.g., to identify threshold patterns or trends, to identify threshold satisfying patterns or trends, etc.), such as increases in temperature, an increasing area/migrating area of temperature increase in one or more arrays of temperature sensors from a catheter insertion site over time, and/or the like. In some non-limiting embodiments, or aspects, dressing and/or securement device 104 (e.g., processor 144, etc.) and/or computing system 106 may filter one or more temperature measurements that fail to satisfy one or more thresholds. For example, shorter term changes in temperature below a threshold may be filtered to prevent false alarms, because catheter infections typically happen over a relatively longer time period.

In some non-limiting embodiments or aspects, dressing and/or securement device 104 (e.g., processor 144, etc.) and/or computing system 106 may analyze one or more temperature measurements to increase a sensitivity and/or a specificity of an alert. For example, larger temperature changes over shorter periods of time may be disregarded or filtered (e.g., if the temperature changes are due to a patient changing clothes, moving a blanket, washing, etc.). As an example, dressing and/or securement device 104 can use pattern matching techniques, machine learning techniques, and/or other algorithms to determine whether there are daily baseline patterns in temperature for a patient to compensate for the daily baseline patterns in determining an alert condition associated with dressing and/or securement device 104 and/or catheter 102.

Further details regarding non-limiting embodiments or aspects of step 310 are provided below with regard to FIGS. 4-7.

As shown in FIG. 3, at step 312, process 300 includes generating an alert. For example, dressing and/or securement device 104 (e.g., processor 144, etc.) and/or computing system 106 may, in response to determining the alert condition, generate an alert to a user. As an example, dressing and/or securement device 104 (e.g., processor 144, etc.) and/or computing system 106 may, in response to determining that at least one threshold temperature is satisfied, generate the alert to the user. For example, dressing and/or securement device 104 (e.g., processor 144, etc.) and/or computing system 106 may, in response to determining that at least one pattern of change satisfies at least one threshold pattern of change, generate, the alert to the user.

In some non-limiting embodiments or aspects, an alert includes information and/or data associated with a potential issue with dressing and/or securement device 104 and/or catheter 102. For example, an alert may include information and/or data associated with a potential or detected peeling of dressing and/or securement device 104, a potential or detected tunneling of dressing and/or securement device 104 (e.g., an air path between a dressing and skin from outside of dressing to interior, etc.), a potential or detected removal of the dressing and/or securement device, an infusion of a fluid, a delivery of a flushing fluid, potential or detected catheter migration, potential or detected catheter extravasation, potential or detected catheter infiltration, and/or the like.

As shown in FIG. 3, at step 314, process 300 includes updating an electronic record. For example, dressing and/or securement device 104 (e.g., processor 144, etc.) and/or computing system 106 may receive user input (e.g., an indication of a removal of dressing and/or securement device 104, an indication to continue monitoring dressing and/or securement device 104, etc.) from a user (e.g., a clinician, etc.) and store the user input in a database in association with the unique identifier associated with dressing and/or securement device 104, the unique identifier of the patient, the unique identifier of catheter 102 and/or a catheter insertion site location of catheter 102 on a body of the patient, and/or other information and/or data associated therewith (e.g., temperature measurements, previous alerts, etc.).

As further shown in FIG. 3, at step 314, process 300 may further include returning to step 302 (e.g., in response to a clinician removing dressing and/or securement device 104, etc.) or returning to and/or continuing the performance of step 308 (e.g., automatically until an indication that dressing and/or securement device 104 has been removed, in response to a clinician providing an indication to continue monitoring dressing and/or securement device 104, etc.).

Figure 4:
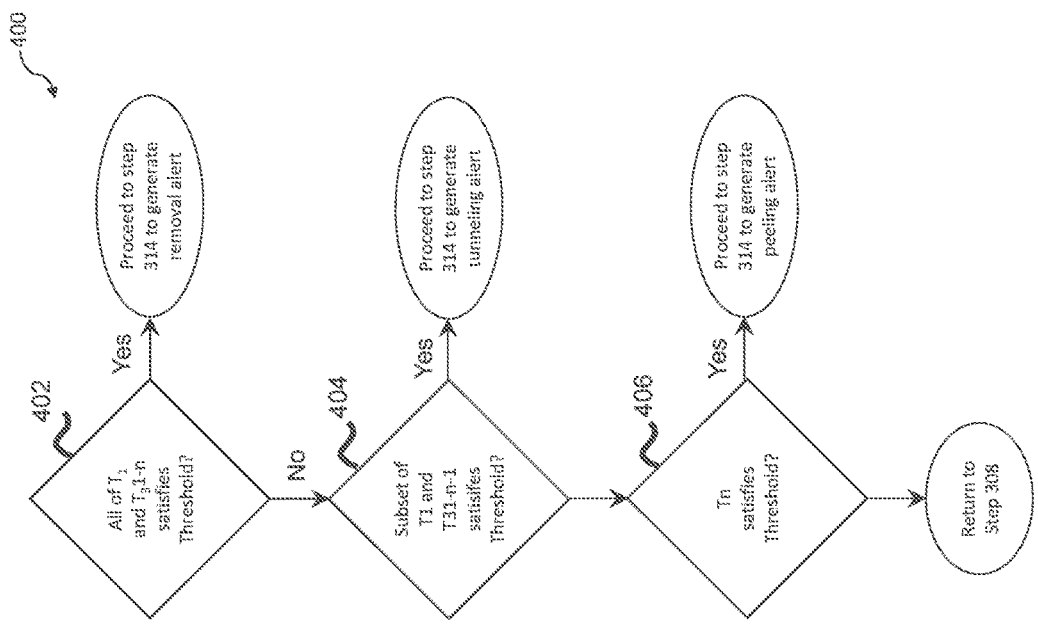
FIG. 4 is a flowchart of non-limiting embodiments or aspects of a process for temperature sensing for intravenous site condition detection.

Referring now to FIG. 4, FIG. 4 is a flowchart of non-limiting embodiments or aspects of a process 400 for intravenous site condition detection. In some non-limiting embodiments or aspects, one or more of the steps of process 400 may be performed (e.g., completely, partially, etc.) by dressing and/or securement device 104. In some non-limiting embodiments or aspects, one or more of the steps of process 400 may be performed (e.g., completely, partially, etc.) by another device or a group of devices separate from or including dressing and/or securement device 104, such as computing system 106 (e.g., one or more devices of computing system 106).

As shown in FIG. 4, at step 402, process 400 includes determining whether each temperature measurement of the first temperature measurement and the plurality of temperature measurements satisfies a threshold temperature. For example, dressing and/or securement device 104 (e.g., processor 144, etc.) and/or computing system 106 may determine whether each temperature measurement of the first temperature measurement (e.g., at $T_1$, etc.) and the plurality of temperature measurements (e.g., at $T_31$ through $T_3n$) satisfies a threshold temperature (e.g., a removal threshold temperature, etc.).

As shown in FIG. 4, if at step 402, dressing and/or securement device 104 (e.g., processor 144, etc.) and/or computing system 106 determines that each temperature measurement of the first temperature measurement (e.g., at $T_1$, etc.) and the plurality of temperature measurements (e.g., at $T_31$ through $T_3n$, etc.) satisfies a threshold temperature (e.g., a removal threshold temperature, etc.), processing may proceed to step 314 of FIG. 3, at which dressing and/or securement device 104 (e.g., processor 144, etc.) and/or computing system 106 may generate, in response to determining that each temperature measurement of the first temperature measurement and the plurality of temperature measurements satisfies the threshold temperature, the alert to the user (e.g., a removal alert, etc.). For example, the alert may include information associated with a potential or detected removal of the dressing and/or securement device.

As shown in FIG. 4, if at step 402, dressing and/or securement device 104 (e.g., processor 144, etc.) and/or computing system 106 determines that each temperature measurement of the first temperature measurement (e.g., at $T_1$, etc.) and the plurality of temperature measurements (e.g., at $T_31$ through $T_3n$, etc.) fails to satisfy a threshold temperature (e.g., a removal threshold temperature, etc.), at step 404, process 400 may include determining whether two or more temperature measurements of the first temperature measurement and the plurality of temperature measurements satisfy a threshold temperature. For example, dressing and/or securement device 104 (e.g., processor 144, etc.) and/or computing system 106 may determine whether two or more temperature measurements of the first temperature measurement (e.g., at $T_1$, etc.) and the plurality of temperature measurements (e.g., at $T_31$ through $T_3n-1$, etc.) satisfy a threshold temperature (e.g., a tunneling threshold temperature, etc.).

As shown in FIG. 4, if at step 404, dressing and/or securement device 104 (e.g., processor 144, etc.) and/or computing system 106 determine that two or more temperature measurements of the first temperature measurement (e.g., at $T_1$, etc.) and the plurality of temperature measurements (e.g., at $T_31$ through $T_3n-1$, etc.) satisfy a threshold temperature (e.g., a tunneling threshold temperature, etc.), processing may proceed to step 314 of FIG. 3, at which dressing and/or securement device 104 (e.g., processor 144, etc.) and/or computing system 106 may generate, in response to determining that the two or more temperature measurements of the first temperature measurement and the plurality of temperature measurements satisfies the threshold temperature, the alert to the user (e.g., a tunneling alert, etc.). For example, the alert may include information associated with a potential or detected tunneling of dressing and/or securement device 104.

As shown in FIG. 4, if at step 404, dressing and/or securement device 104 (e.g., processor 144, etc.) and/or computing system 106 determine that two or more temperature measurements of the first temperature measurement (e.g., at $T_1$, etc.) and the plurality of temperature measurements (e.g., at $T_31$ through $T_3n-1$, etc.) fails to satisfy a threshold temperature (e.g., a tunneling threshold temperature, etc.), at step 406, process 400 may include determining whether a temperature measurement of the plurality of temperature measurements at a most distant location of the plurality of locations from the first location satisfies a threshold temperature. For example, dressing and/or securement device 104 (e.g., processor 144, etc.) and/or computing system 106 may determine whether a temperature measurement of the plurality of temperature measurements at a most distant location of the plurality of locations from the first location (e.g., at $T_3n$, etc.) satisfies a threshold temperature (e.g., a peeling threshold temperature, etc.).

As shown in FIG. 4, if at step 406, dressing and/or securement device 104 (e.g., processor 144, etc.) and/or computing system 106 determine that a temperature measurement of the plurality of temperature measurements at a most distant location of the plurality of locations from the first location (e.g., at $T_3n$, etc.) satisfies a threshold temperature (e.g., a peeling threshold temperature, etc.), processing may proceed to step 314 of FIG. 3, at which dressing and/or securement device 104 (e.g., processor 144, etc.) and/or computing system 106 may generate, in response to determining that the temperature measurement at the most distant location of the plurality of locations from the first location satisfies the threshold temperature, the alert to the user (e.g., a peeling alert, etc.). For example, the alert may include information associated with a potential or detected peeling of dressing and/or securement device 104.

Accordingly, non-limiting embodiments or aspects of the present disclosure may provide for detection of compromised dressings and/or securement devices by sensing temperature differences and/or temperatures lower than a threshold temperature (e.g., lower than a body temperature, etc.) as indications a dressing and/or securement device is no longer affixed to the patient, tunneling, and/or peeling, and/or detection of catheter migration (e.g., partial or complete dislodgement, etc.) through sensing of temperature changes (e.g., temperature changes adjacent or at catheter insertion site or on portions of catheter at insertion site, etc.).

Figure 5:
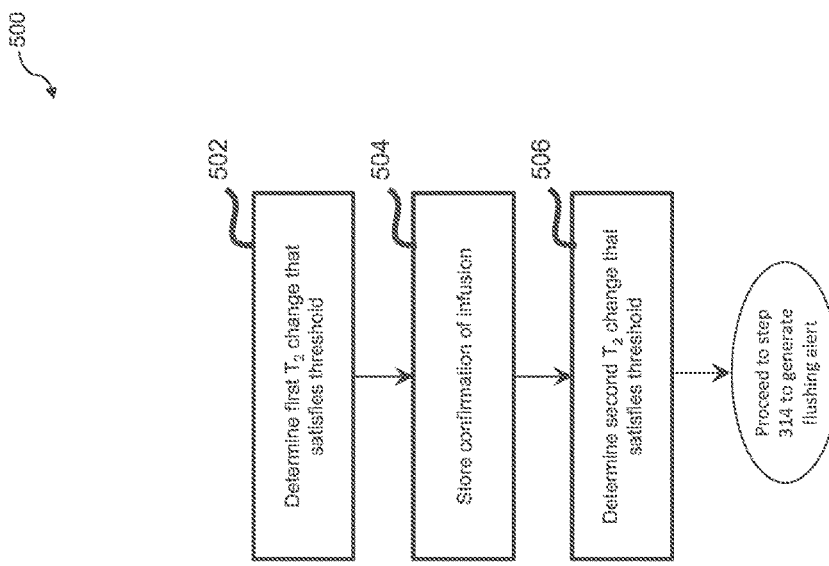
FIG. 5 is a flowchart of non-limiting embodiments or aspects of a process for temperature sensing for intravenous site condition detection.

Referring now to FIG. 5, FIG. 5 is a flowchart of non-limiting embodiments or aspects of a process 500 for intravenous site condition detection. In some non-limiting embodiments or aspects, one or more of the steps of process 500 may be performed (e.g., completely, partially, etc.) by dressing and/or securement device 104. In some non-limiting embodiments or aspects, one or more of the steps of process 500 may be performed (e.g., completely, partially, etc.) by another device or a group of devices separate from or including dressing and/or securement device 104, such as computing system 106 (e.g., one or more devices of computing system 106).

As shown in FIG. 5, at step 502, process 500 includes determining that a first change over time in the second temperature satisfies an infusion temperature threshold. For example, dressing and/or securement device 104 (e.g., processor 144, etc.) and/or computing system 106 may determine that a first change over time in the second temperature (e.g., at $T_2$, etc.) satisfies an infusion temperature threshold.

As shown in FIG. 5, at step 504, process 500 includes, in response to determining that a first change over time in the second temperature (e.g., at $T_2$, etc.) satisfies an infusion temperature threshold, storing a confirmation of an infusion operation in association with a record of the patient. For example, dressing and/or securement device 104 (e.g., processor 144, etc.) and/or computing system 106 may store, in a database, a confirmation of an infusion operation in association with a record of the patient.

As shown in FIG. 5, at step 506, process 500 includes determining a second change over time in the second temperature subsequent to the first change that satisfies a flush temperature threshold. For example, dressing and/or securement device 104 (e.g., processor 144, etc.) and/or computing system 106 may determine a second change over time in the second temperature (e.g., at $T_2$, etc.) subsequent to the first change that satisfies a flush temperature threshold. As shown in FIG. 5, in response to determining a second change over time in the second temperature (e.g., at $T_2$, etc.) subsequent to the first change that satisfies a flush temperature threshold, processing may proceed to step 314 of FIG. 3, at which dressing and/or securement device 104 (e.g., processor 144, etc.) and/or computing system 106 may generate, the alert to the user. For example, the alert includes a prompt to the user to confirm delivery of a flushing fluid, and upon receipt of the confirmation from the user, dressing and/or securement device 104 (e.g., processor 144, etc.) and/or computing system 106 may store the confirmation, in a database, in association with a record of the patient.

Figure 6:
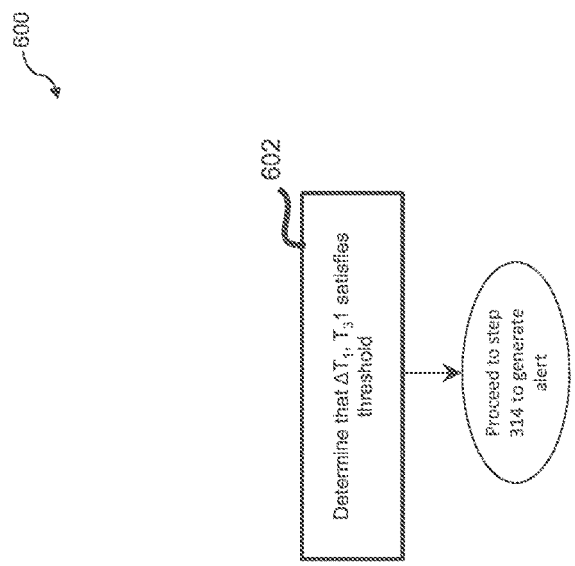
FIG. 6 is a flowchart of non-limiting embodiments or aspects of a process for temperature sensing for intravenous site condition detection.

Referring now to FIG. 6, FIG. 6 is a flowchart of non-limiting embodiments or aspects of a process 600 for intravenous site condition detection. In some non-limiting embodiments or aspects, one or more of the steps of process 600 may be performed (e.g., completely, partially, etc.) by dressing and/or securement device 104. In some non-limiting embodiments or aspects, one or more of the steps of process 600 may be performed (e.g., completely, partially, etc.) by another device or a group of devices separate from or including dressing and/or securement device 104, such as computing system 106 (e.g., one or more devices of computing system 106).

As shown in FIG. 6, at step 602, process 600 includes determining that a change between the first temperature measurement and a temperature measurement of the plurality of temperature measurements at the closest location of the plurality of locations to the first location satisfies a threshold temperature. For example, dressing and/or securement device 104 (e.g., processor 144, etc.) and/or computing system 106 may determine that a change between the first temperature measurement (e.g., at $T_1$, etc.) and a temperature measurement of the plurality of temperature measurements at the closest location of the plurality of locations to the first location (e.g., at $T_31$, etc.) satisfies a threshold temperature. For example, the first location and a closest location of the plurality of locations to the first location may be located at a same distance from a catheter tubing of catheter 102 and a same distance from the catheter insertion site of catheter 102 on the body of the patient. As an example, first temperature sensor $T_1$ and a closest temperature sensor of the array of temperature sensors to the first temperature sensor (e.g., $T_31$, etc.) may be located at a same distance from a catheter tubing of catheter 102 and a same distance from the catheter insertion site of catheter 102 on the body of the patient.

As shown in FIG. 6, in response to determining that a change between the first temperature measurement (e.g., at $T_1$, etc.) and a temperature measurement of the plurality of temperature measurements at the closest location of the plurality of locations to the first location (e.g., at $T_31$, etc.) satisfies a threshold temperature, processing may proceed to step 314 of FIG. 3, at which dressing and/or securement device 104 (e.g., processor 144, etc.) and/or computing system 106 may generate, the alert to the user. For example, the alert may include information associated with a potential issue with the dressing and/or securement device and/or the catheter.

Figure 7:
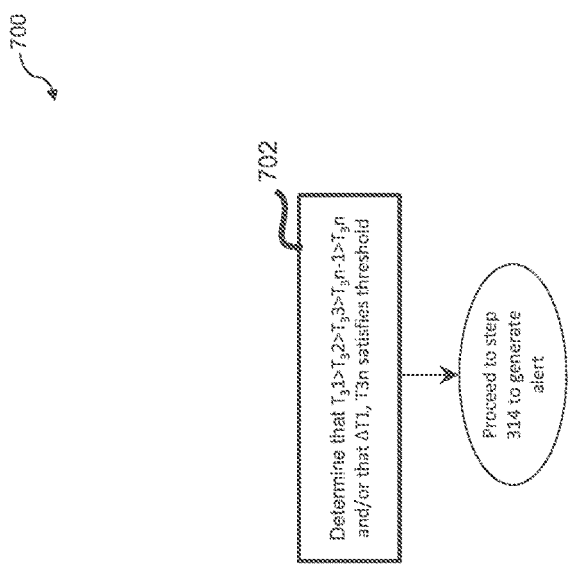
FIG. 7 is a flowchart of non-limiting embodiments or aspects of a process for temperature sensing for intravenous site condition detection.

Referring now to FIG. 7, FIG. 7 is a flowchart of non-limiting embodiments or aspects of a process 700 for intravenous site condition detection. In some non-limiting embodiments or aspects, one or more of the steps of process 700 may be performed (e.g., completely, partially, etc.) by dressing and/or securement device 104. In some non-limiting embodiments or aspects, one or more of the steps of process 700 may be performed (e.g., completely, partially, etc.) by another device or a group of devices separate from or including dressing and/or securement device 104, such as computing system 106 (e.g., one or more devices of computing system 106).

As shown in FIG. 7, at step 702, process 700 includes determining at least one of (i) an increase in temperatures of temperature measurements from a most distant location of the plurality of locations to the first temperature measurement and (ii) an increase in a temperature difference between the first temperature measurement and a temperature measurement at the most distant location of the plurality of locations to the first temperature measurement that satisfies a threshold temperature increase. For example, dressing and/or securement device 104 (e.g., processor 144, etc.) and/or computing system 106 may determine at least one of (i) an increase in temperatures of temperature measurements from a most distant location of the plurality of locations to the first temperature measurement (e.g., $T_31 > T_32 > T_33 > T_3n-1 > T_3n$, etc.) and (ii) an increase in a temperature difference between the first temperature measurement and a temperature measurement at the most distant location of the plurality of locations to the first temperature measurement (e.g., $\Delta T1$, $T3n$, etc.) that satisfies a threshold temperature increase.

As shown in FIG. 7, in response to determining at least one of (i) an increase in temperatures of temperature measurements from a most distant location of the plurality of locations to the first temperature measurement and (ii) an increase in a temperature difference between the first temperature measurement and a temperature measurement at the most distant location of the plurality of locations to the first temperature measurement that satisfies a threshold temperature increase, processing may proceed to step 314 of FIG. 3, at which dressing and/or securement device 104 (e.g., processor 144, etc.) and/or computing system 106 may generate, the alert to the user. For example, the alert may include information associated with a potential issue with the dressing and/or securement device and/or the catheter. As an example, if temperature changes indicating warming at a site beyond a defined criteria suggesting potential phlebitis and/or infection of the site (e.g., absolute temperature increasing toward catheter insertion site from an edge of support member 140, $T_31 > T_32 > T_33 > T_3n-1 > T_3n$ etc. and/or temporal patterns in temperature differences increasing over time, $\Delta T1$, $T3n$ increasing over time, etc.), an alert may be sent to a clinician to check the catheter insertion site for potential complications. In some non-limiting embodiments or aspects, dressing and/or securement device 104 (e.g., processor 144, etc.) and/or computing system 106 may account for (e.g., filter, etc.) temporal elements associated with limited transient warming upon initial catheter placement.

Figure 8:
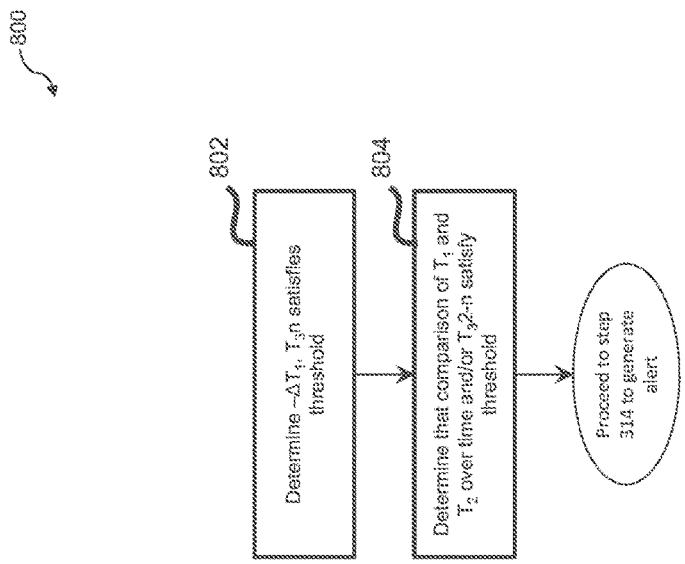
FIG. 8 is a flowchart of non-limiting embodiments or aspects of a process for temperature sensing for intravenous site condition detection.

Referring now to FIG. 8, FIG. 8 is a flowchart of non-limiting embodiments or aspects of a process 800 for intravenous site condition detection. In some non-limiting embodiments or aspects, one or more of the steps of process 800 may be performed (e.g., completely, partially, etc.) by dressing and/or securement device 104. In some non-limiting embodiments or aspects, one or more of the steps of process 800 may be performed (e.g., completely, partially, etc.) by another device or a group of devices separate from or including dressing and/or securement device 104, such as computing system 106 (e.g., one or more devices of computing system 106).

As shown in FIG. 8, at step 802, process 800 includes determining that a decrease in temperature between the first location and a most distant location of the plurality of locations from the first location satisfies a threshold temperature. For example, dressing and/or securement device 104 (e.g., processor 144, etc.) and/or computing system 106 may determine that a decrease in temperature between the first location (e.g., at $T_1$, etc.) and a most distant location of the plurality of locations from the first location (e.g., at $T_3n$, etc.) satisfies a threshold temperature. As shown in FIG. 8, in response to determining that a decrease in temperature between the first location (e.g., at $T_1$, etc.) and a most distant location of the plurality of locations from the first location (e.g., at $T_3n$, etc.) satisfies a threshold temperature, dressing and/or securement device 104 (e.g., processor 144, etc.) and/or computing system 106 may determine that a comparison of the first temperature measurement (e.g., at $T_1$, etc.) and at least one of the following: (i) the second temperature measurement (e.g., at $T_2$, etc.) at a current time and at least one time prior to the current time and (ii) a temperature measurement of a location of the plurality of locations more distant from the catheter insertion site than the first location (e.g., at $T_32$ through $T_3n$, etc.), satisfy at least one threshold temperature.

As shown in FIG. 8, in response to determining that a decrease in temperature between the first location (e.g., at $T_1$, etc.) and a most distant location of the plurality of locations from the first location (e.g., at $T_3n$, etc.) satisfies a threshold temperature, dressing and/or securement device 104 (e.g., processor 144, etc.) and/or computing system 106 may determine that a comparison of the first temperature measurement (e.g., at $T_1$, etc.) and at least one of the following: (i) the second temperature measurement (e.g., at $T_2$, etc.) at a current time and at least one time prior to the current time and (ii) a temperature measurement of a location of the plurality of locations more distant from the catheter insertion site than the first location (e.g., at $T_32$ through $T_3n$, etc.), satisfy at least one threshold temperature, processing may proceed to step 314 of FIG. 3, at which dressing and/or securement device 104 (e.g., processor 144, etc.) and/or computing system 106 may generate, the alert to the user. For example, the alert may include information associated with a potential issue with the dressing and/or securement device and/or the catheter. As an example, if a temperature change is sensed that suggests infiltration, extravasation, and/or catheter dislodgement, a decrease in temperature between $T_1$ (and/or $T_31$) and $T_n$, T1 (and/or $T_31$) may be compared to $T_2$ at a current time and a time prior to the current time (e.g., prior to the temperature change, etc.) to determine whether cooling is caused by a change in the temperature of the fluid being infused (as opposed to a complication). In such an example, if the cooling is not coincident (and not shortly following) with a cooling of the infusion fluid as measured at $T_2$ or if the cooling extends beyond a defined distance as defined by temperature sensors $T_31$ through $T_3n$ (e.g., if the cool has reached temperature sensor $T_33$, etc.), an alert may be sent to the clinician to check the catheter insertion site for potential complications. In some non-limiting embodiments or aspects, these distance and temperature change threshold may account for a time since a temperature change in the infusion fluid and an expected amount of temperature change based on thermal diffusion rates and cellular thermal energy output at the catheter insertion site. Accordingly, non-limiting embodiments or aspects of the present disclosure may provide for detection catheter migration including partial or complete dislodgement of a catheter through sensing of temperature changes (e.g., temperature changes around or near the catheter insertion site and/or on portions of a catheter at the catheter insertion site, etc.), detection of catheter extravasation, creation of data useful for monitoring workflows, automating documentation, and/or detecting patients self-administering medications (e.g., in the case of a rapid infusion from a flush syringe, or a medication push from a syringe, the dressing can sense a reduction in temperature on initiation and a rise in temperature on completion of the dose), and/or the like.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, any of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. A dressing and/or securement device for a catheter, comprising:
a support member configured to receive a portion of the catheter therethrough, the support member including:
a first temperature sensor configured to obtain a first temperature measurement at a first location on a body of a patient adjacent a catheter insertion site of the catheter; and an array of temperature sensors configured to obtain a plurality of temperature measurements at a plurality of locations on the body of the patient, wherein each temperature sensor of the array of temperature sensors is spaced apart from the first temperature sensor on the support member, and wherein the array of temperature sensors comprises temperature sensors at a plurality of different distances from the first temperature sensor;

a wired or wireless communication device configured to communicate the first temperature measurement and the plurality of temperature measurements; and one or more processors configured to receive the first temperature measurement and the plurality of temperature measurements from the wired or wireless communication device, wherein the one or more processors are programmed and/or configured to:

determine a plurality of first temperature differences between the first temperature measurement and each of the plurality of temperature measurements;

determine, based on the plurality of first temperature differences, an alert condition associated with the dressing and/or securement device for the catheter and/or the catheter; and in response to the determination of the alert condition, generate an alert for transmission to a device.

2. The dressing and/or securement device of claim 1, wherein to determine the alert condition, the one or more processors are further programmed and/or configured to:

determine a plurality of second temperature differences between (i) a temperature measurement of the plurality of temperature measurements at a most distant temperature sensor of the array of temperature sensors from the first temperature sensor and (ii) each remaining temperature measurement of the plurality of temperature measurements at each remaining temperature sensor of the array of temperature sensors;

determine at least one threshold temperature based on the plurality of first temperature differences and the plurality of second temperature differences;

determine that the first temperature measurement, one or more temperature measurements of the plurality of temperature measurements, or any combination thereof, satisfies the at least one threshold temperature; and in response to the determination that the at least one threshold temperature is satisfied, generate the alert to the device.

3. The dressing and/or securement device of claim 1, wherein to determine the alert condition, the one or more processors are further programmed and/or configured to:

determine that a temperature measurement of the plurality of temperature measurements at a most distant temperature sensor of the array of temperature sensors from the first temperature sensor satisfies a threshold temperature; and in response to the determination that the temperature measurement of the most distant temperature sensor of the array of temperature sensors from the first temperature sensor satisfies the threshold temperature, generate the alert to the device, wherein the alert includes information associated with a potential peeling of the dressing and/or securement device.

4. The dressing and/or securement device of claim 1, wherein to determine the alert condition, the one or more processors are further programmed and/or configured to:

determine that two or more temperature measurements of the first temperature measurement and the plurality of temperature measurements satisfy a threshold temperature; and in response to the determination that the two or more temperature measurements of the first temperature measurement and the plurality of temperature measurements satisfy the threshold temperature, generate the alert to the device, wherein the alert includes information associated with a potential tunneling of the dressing and/or securement device.

5. The dressing and/or securement device of claim 1, wherein to determine the alert condition, the one or more processors are further programmed and/or configured to:

determine that each temperature measurement of the first temperature measurement and the plurality of temperature measurements satisfies a threshold temperature; and in response to the determination that each temperature measurement of the first temperature measurement and the plurality of temperature measurements satisfies the threshold temperature, generate the alert to the device, wherein the alert includes information associated with a potential removal of the dressing and/or securement device.

6. The dressing and/or securement device of claim 1, wherein the support member further includes a second temperature sensor, wherein the second temperature sensor is configured to obtain a second temperature measurement at a catheter tubing of the catheter, wherein the second temperature sensor is spaced apart from the first temperature sensor and the array of temperature sensors on the support member, and wherein to determine the alert condition, the one or more processors are further programmed and/or configured to:

determine that a first change over time in the second temperature measurement satisfies an infusion temperature threshold;

store a confirmation of an infusion operation in association with a record of the patient;

determine a second change over time in the second temperature measurement subsequent to the first change that satisfies a flush temperature threshold; and in response to the determination that the second change over time in the second temperature measurement satisfies the flush temperature threshold, generate the alert to the device, wherein the alert includes a prompt to a user to confirm delivery of a flushing fluid.

7. The dressing and/or securement device of claim 1, wherein to determine the alert condition, the one or more processors are further programmed and/or configured to:

determine that at least one pattern of change in at least one of the following: the first temperature measurement, one or more temperature measurements of the plurality of temperature measurements, or any combination thereof, satisfies at least one threshold pattern of change; and in response to the determination that the at least one pattern of change satisfies the at least one threshold pattern of change, generate the alert to the device, wherein the alert includes information associated with a potential issue with the dressing and/or securement device and/or the catheter.

8. The dressing and/or securement device of claim 7, wherein the at least one pattern of change includes a change over time in one or more individual temperature measurements of the first temperature measurement and the plurality of temperature measurements.

9. The dressing and/or securement device of claim 7, wherein the at least one pattern of change includes a change over time in a temperature difference between two or more temperature measurements of the first temperature measurement and the plurality of temperature measurements.

10. The dressing and/or securement device of claim 7, wherein the one or more processors are further programmed and/or configured to:
determine the at least one threshold pattern of change based on at least one of the following: a patient parameter associated with the patient, a medication parameter associated with a medication delivered, being delivered, or to be delivered to the patient, a care environment parameter associated with a care environment in which the patient is located, or any combination thereof.

11. The dressing and/or securement device of claim 1, wherein the support member includes a marking or an opening indicating the catheter insertion site of the catheter on the body of the patient, and wherein the first temperature sensor and a closest temperature sensor of the array of temperature sensors to the first temperature sensor are located at a same distance from the marking or the opening, and wherein to determine the alert condition, the one or more processors are further programmed and/or configured to:
determine that a change between the first temperature measurement and a temperature measurement of the plurality of temperature measurements at the closest temperature sensor of the array of temperature sensors to the first temperature sensor satisfies a threshold temperature; and
in response to the determination that the change between the first temperature measurement and the temperature measurement of the plurality of temperature measurements at the closest temperature sensor of the array of temperature sensors to the first temperature sensor satisfies the threshold temperature, generate, with the one or more processors, the alert to the device, wherein the alert includes information associated with a potential issue with the dressing and/or securement device and/or the catheter.

12. The dressing and/or securement device of claim 1, wherein to determine the alert condition, the one or more processors are further programmed and/or configured to:
determine at least one of (i) an increase in a temperature measurements of the plurality of temperature measurements at a most distant temperature sensor of the array of temperature sensors to the first temperature measurement or (ii) an increase in a temperature difference between the first temperature measurement and the temperature measurement at the most distant temperature sensor of the array of temperature sensors to the first temperature measurement that satisfies a threshold temperature increase; and
in response to the determination of at least one of (i) or (ii), generate, with the one or more processors, the alert to the device, wherein the alert includes information associated with a potential issue with the dressing and/or securement device and/or the catheter.

13. The dressing and/or securement device of claim 1, wherein the support member further includes a second temperature sensor, wherein the second temperature sensor is configured to obtain a second temperature measurement at a catheter tubing of the catheter, wherein the second temperature sensor is spaced apart from the first temperature sensor and the array of temperature sensors on the support member, and wherein to determine the alert condition, the one or more processors are further programmed and/or configured to:
determine that a decrease in temperature between the first temperature sensor and a most distant temperature sensor of the array of temperature sensors from the first temperature sensor satisfies at least one threshold temperature;
in response to the determination that the decrease in temperature satisfies the at least one threshold temperature, determine that a comparison of the first temperature measurement and at least one of the following: (i) the second temperature measurement at a current time and at least one time prior to the current time or (ii) a temperature measurement of the plurality of temperature measurements at a temperature sensor of the array of temperature sensors more distant from the catheter insertion site than the first temperature sensor, satisfy the at least one threshold temperature; and
in response to the determination that the at least one threshold temperature is satisfied, generate the alert to the device, wherein the alert includes information associated with a potential issue with the dressing and/or securement device and/or the catheter.

14. The dressing and/or securement device of claim 1, wherein the first temperature measurement and the plurality of temperature measurements are obtained at a periodic rate, and wherein the one or more processors are further programmed and/or configured to:
determine the periodic rate based on at least one of the following: a patient parameter associated with the patient, a medication parameter associated with a medication delivered, being delivered, or to be delivered to the patient, or any combination thereof.

15. The dressing and/or securement device of claim 1, wherein the dressing and/or securement device further includes a plurality of arrays of temperature sensors including the array of temperature sensors, wherein the plurality of arrays of temperature sensors are configured to obtain the plurality of temperature measurements at the plurality of locations on the body of the patient, and wherein the plurality of arrays of temperature sensors are spaced apart about the support member.

16. The dressing and/or securement device of claim 15, wherein the plurality of arrays of temperature sensors are spaced apart around a circumference of a circle defined within a plane of the support member, and wherein temperature sensors of the plurality of arrays of temperature sensors associated with individual arrays of the plurality of arrays of temperature sensors are spaced apart radially at a plurality of different distances from a center of the circle.

17. The dressing and/or securement device of claim 15, wherein an array of the plurality of arrays of temperature sensors includes the first temperature sensor.

18. The dressing and/or securement device of claim 1, wherein the dressing and/or securement device includes a marking or an opening indicating an orientation of the support member for attachment at the catheter insertion site of the catheter on the body of the patient.

19. The dressing and/or securement device of claim 1, wherein the support member further includes an adhesive layer configured to secure at least the portion of the catheter to the catheter insertion site.

20. The dressing and/or securement device of claim 1, wherein the support member includes an antimicrobial disk with an opening therethrough configured to receive at least the portion of the catheter.

* * * * *